(12) United States Patent
Lee et al.

(10) Patent No.: US 10,213,149 B2
(45) Date of Patent: Feb. 26, 2019

(54) SYSTEMS AND METHODS FOR ASSESSING HUMAN COGNITION, INCLUDING A QUANTITATIVE APPROACH TO ASSESSING EXECUTIVE FUNCTION

(71) Applicant: Medical Care Corporation, Newport Beach, CA (US)

(72) Inventors: Michael D. Lee, Irvine, CA (US); William Rodman Shankle, Corona del Mar, CA (US)

(73) Assignee: Medical Care Corporation, Newport Beach, CA (US)

( * ) Notice: Subject to any disclaimer, the term of this patent is extended or adjusted under 35 U.S.C. 154(b) by 0 days.

(21) Appl. No.: 15/309,419

(22) PCT Filed: May 8, 2015

(86) PCT No.: PCT/US2015/029883
§ 371 (c)(1),
(2) Date: Nov. 7, 2016

(87) PCT Pub. No.: WO2015/172017
PCT Pub. Date: Nov. 12, 2015

(65) Prior Publication Data
US 2017/0181685 A1 Jun. 29, 2017

Related U.S. Application Data

(60) Provisional application No. 61/990,550, filed on May 8, 2014.

(51) Int. Cl.
*A61B 5/00* (2006.01)
*A61B 5/0484* (2006.01)
(Continued)

(52) U.S. Cl.
CPC ............. *A61B 5/4088* (2013.01); *A61B 5/16* (2013.01); *A61B 5/165* (2013.01); *A61B 5/168* (2013.01);
(Continued)

(58) Field of Classification Search
CPC ....... A61B 5/4088; A61B 5/165; A61B 5/168; G06F 19/3437; G06F 19/345;
(Continued)

(56) References Cited

U.S. PATENT DOCUMENTS 6,225,920 B1 5/2001 Dayle
6,280,198 B1 8/2001 Calhoun et al.
(Continued)

FOREIGN PATENT DOCUMENTS

EP 1139268 10/2001
EP 1323377 7/2003
(Continued)

OTHER PUBLICATIONS

Au et al. (2003) "Conceptual Organization in Alzheimer's Dementia", Journal of Clinical and Experimental Neuropsychology, 25:6, 737-750.
(Continued)

*Primary Examiner* — Ly D Pham
(74) *Attorney, Agent, or Firm* — Fish & Richardson P.C.

(57) ABSTRACT

Methods, systems, and apparatus, including medium-encoded computer program products, for analyzing data include: receiving data including a person's responses regarding judgments of semantic similarities between items selected from a group of items falling into a same categorical level; processing the data to determine a measure of distance within a generated representation of the person's responses regarding the judgments of semantic similarities; and generating a score of degree of cognitive impairment for the
(Continued)

person based at least in part on the determined measure of distance within the generated representation.

25 Claims, 14 Drawing Sheets

(51) Int. Cl.

| | |
|---|---|
| *G06F 19/00* | (2018.01) |
| *G16H 50/50* | (2018.01) |
| *G16H 50/20* | (2018.01) |
| *A61B 5/16* | (2006.01) |
| *G06K 9/62* | (2006.01) |
| *G06N 5/02* | (2006.01) |
| *G06N 5/04* | (2006.01) |
| *G16H 50/70* | (2018.01) |
| *G06F 17/27* | (2006.01) |
| *G16H 50/30* | (2018.01) |

(52) U.S. Cl.
CPC ............ *A61B 5/7264* (2013.01); *G06F 19/00* (2013.01); *G06K 9/6251* (2013.01); *G06N 5/025* (2013.01); *G06N 5/043* (2013.01); *G06N 5/046* (2013.01); *G16H 50/20* (2018.01); *G16H 50/50* (2018.01); *G06F 17/2785* (2013.01); *G16H 50/30* (2018.01); *G16H 50/70* (2018.01)

(58) Field of Classification Search
CPC ...... G06K 9/6251; G06N 5/025; G06N 5/043; G06N 5/046
USPC .......................................................... 706/52
See application file for complete search history.

(56) References Cited

U.S. PATENT DOCUMENTS

| | | | |
|---|---|---|---|
| 6,820,037 | B2 | 11/2004 | Simon |
| 6,884,078 | B2 | 4/2005 | Wiig et al. |
| 7,294,107 | B2 | 11/2007 | Simon et al. |
| 7,311,666 | B2 | 12/2007 | Stupp et al. |
| 7,363,299 | B2 | 4/2008 | Dalvi et al. |
| 7,689,272 | B2 | 3/2010 | Farwell |
| 7,837,472 | B1 | 11/2010 | Elsmore et al. |
| 8,202,095 | B2 | 6/2012 | Shankle et al. |
| 8,412,664 | B2 | 4/2013 | Shankle |
| 9,367,666 | B2 | 6/2016 | Shankle et al. |
| 2002/0016531 | A1 | 2/2002 | Buschke |
| 2003/0073885 | A1 | 4/2003 | Theodoracopulos et al. |
| 2005/0102171 | A1 | 5/2005 | Ashley et al. |
| 2005/0142524 | A1 | 6/2005 | Simon et al. |
| 2005/0143630 | A1 | 6/2005 | Darby et al. |
| 2005/0187436 | A1 | 8/2005 | Doniger et al. |
| 2005/0196735 | A1 | 9/2005 | Buschke |
| 2006/0252014 | A1 | 11/2006 | Simon et al. |
| 2007/0100251 | A1 | 5/2007 | Prichep |
| 2008/0114564 | A1 | 5/2008 | Ihara |
| 2008/0280276 | A1 | 11/2008 | Raber et al. |
| 2009/0155754 | A1 | 6/2009 | Shankle et al. |
| 2009/0313047 | A1 | 12/2009 | Smith et al. |
| 2011/0028827 | A1 | 2/2011 | Sitaram et al. |
| 2011/0060715 | A1 | 3/2011 | Shankle |
| 2013/0191153 | A1 | 7/2013 | Lee et al. |
| 2015/0216414 | A1* | 8/2015 | Wood ............ G09B 7/00 600/303 |

FOREIGN PATENT DOCUMENTS

| | | |
|---|---|---|
| JP | 2002078699 | 3/2002 |
| KR | 2005-054149 | 6/2005 |
| WO | WO 2002/005247 | 1/2002 |
| WO | WO2014/052938 | 4/2014 |

OTHER PUBLICATIONS

Bakker et al., "Bayesian Metric Multidimensional Scaling", Political Analysis (2013) 21:125-140.

Bayles et al., "Naming and Categorical Knowledge in Alzheimer's Disease: The Process of Semantic Memory Deterioration", Brain and Language 39, 498-510 (1990).

Bousfield, W.A., "The Occurrence of Clustering in the Recall of Randomly Arranged Associates", The Journal of General Psychology, 1953, 49, 229-240.

Brooks et al., "General Methods for Monitoring Convergence of Iterative Simulations", Journal of Computational and Graphical Statistics, vol. 7, No. 4, pp. 434-455, 1998.

Burton et al., "Balanced Designs for Triads Tests: Two Examples from English", Social Science Research 5, 247-267 (1976).

Chan et al., "Comparison of the Semantic Networks in patients with Dementia and Amnesia", Neuropsychology 1995, vol. 9, No. 2, 177-186.

Chan et al., "Abnormal Semantic Network for 'Animals' But Not 'Tools' in Patients with Alzheimer's Disease", Cortex (2001) 37, 197-217.

Clark et al., "Distance to Nearest Neighbor as a Measure of Spatial Relationships in Populations", Ecology, vol. 35, Issue 4 (Oct. 1954), 445-453.

Dong et al., Weighted-Edge based Similarity Measurement Tools for Word Semantics, IEEE/WIC/AM International Conference, vol. 1, 2010.

Dry et al., "Clustering, Randomness, and Regularity: Spatial Distributions and Human Performance on the Traveling Salesperson Problem and Minimum Spanning Tree Problem", The Journal of Problem Solving, vol. 4, No. 1 (2012), 1-17.

Fagundo et al., "Clustering and switching in semantic fluency: predictors of the development of Alzheimer's disease", International Journal of Geriatric Psychiatry 2008; 23:1007-1013.

Kruschke, John K., "ALCOVE: An Exemplar-Based Connectionist Model of Category Learning", Psychological Review 1992, vol. 99, No. 1, 22-44.

Lee, M.D., "How cognitive modeling can benefit from hierarchical Bayesian models", vol. 55, 2011.

Moore et al., "Cultural, Gender, and Individual Differences in Perceptual and Semantic Structures of Basic Colors in Chinese and English", Journal of Cognition and Culture 2.1, 2002, 1-28.

Navarro et al., "Common and distinctive features in stimulus similarity: A modified version of the contrast model", Psychomonic Bulletin & Review 2004, 11 (6), 961-974.

Nosofsky, Robert M., "Choice, Similarity, and the context Theory of Classification", Journal of Experimental Psychology: Learning, Memory, and Cognition 1984, vol. 1, No. 1, 104-114.

Nosofsky, Robert M., "Attention, Similarity, and the Identification-Categorization Relationship", Journal of Experimental Psychology: General, 1986, vol. 115, No. 1, 39-57.

Nosofsky, Robert M., "Similarity Scaling and Cognitive Process Models", Annu. Rev. Psychol. 1992, 43:25-53.

Plummer, Martyn, "JAGS: A program for analysis of Bayesian graphical models using Gibbs sampling", DSC 2003 Working Papers, http://www.ci/tuwien.ac.at/Conferences/DSC-2003/, pp. 1-8.

Romney et al., "Predicting Clustering From Semantic Structure", Psychological Science, American Psychological Society, vol. 4, No. 1, Jan. 1993, pp. 28-34.

Romney et al., "Toward a Theory of Culture as Shared Cognitive Structures", Ethos 26(3): 314-337, 1998.

Romney et al., "Systemic Culture Patterns as Basic Units of Cultural Transmission and Evolution", Cross-Cultural Research, vol. 35, No. 2, May 2001, 154-178.

Schvaneveldt et al., "Network Structures in Proximity Data", The Psychology of Learning and Motivation, vol. 24, 1989, pp. 249-284.

Shepard, Roger N., "Representation of Structure in Similarity Data: Problems and Prospects", Psychometrika, vol. 39, No. 4, Dec. 1974, pp. 373-421.

Shepard, Roger N., "Multidimensional Scaling, Tree-Fitting, and Clustering", Science, New Series, vol. 210, Issue 4468 (Oct. 24, 1980), 390-398.

(56) References Cited

OTHER PUBLICATIONS

Shepard, Roger N., "Toward a Universal Law of Generalization for Psychological Science", Science, New Series, vol. 237, No. 4820 (Sep. 11, 1987), pp. 1217-1323.
Silveri et al., "Dissociation between knowledge of living and nonliving things in dementia of the Alzheimer type", Neurology 41, Apr. 1991, pp. 545-546.
Simmons et al., "Left inferior prefrontal cortex activation during a semantic decision-making task predicts the degree of semantic organization", NeuroImage 28 (2005) 30-38.
Sylvester et al., "Evidence for Intact Semantic Representations in patients With Frontal Lobe Lesions", Neuropsychology 2002, vol. 16, No. 2, 197-207.
Tallent et al., "Associating Semantic Space Abnormalities With Formal Thought Disorder in Schizophrenia: Use of Triadic Comparisons", Journal of Clinical and Experimental Neuropsychology, 23:3, 285-296.
Thurston, L.L., "A Law of Comparative Judgment", Psychological Review 1994, vol. 101, No. 2, 266-270.
Troyer et al., "Clustering and Switching as Two Components of Verbal Fluency: Evidence From Younger and Older Healthy Adults", vol. 11, No. 1, 1997, pp. 145-146.
Van Ravenzwaaij et al., "Cognitive model decomposition of the BART: Assessment and application", Journal of mathematical psychology 55 (2011) 94-105.
Wetzels et al., "Bayesian parameter estimation in the Expectancy Valence model of the Iowa gambling task", Journal of Mathematical Psychology 54 (2010) 14-27.
Zhou et al., "Abnormal connectivity in the posterior cingulate and hippocampus in early Alzheimer's disease and mild cognitive impairment", Alzheimer's & Dementia, vol. 4, 2008, pp. 266-269.
International Application No. PCT/US15/29883, Notification of Transmittal of the International Search Report and the Written opinion of the International Searching Authority, dated Aug. 7, 2015.
U.S. Appl. No. 11/957,326, filed Dec. 14, 2007, in Office Action dated Feb. 24, 2011, 26 pages.
Barclay, "Enhanced Recognition of Defectors Depends on Their Rarity," 2008, ScienceDirect, pp. 817-828, 12 pages.
Buyse et al., "The Role of Biostatistics in the Prevention, Detection and Treatment of Fraud in Clinical Trials," 1999, Statistics in Medicine, vol. 18, 3435-3451, 17 pages.
Cho et al., "Early Detection and Diagnosis of MCI Using the MCI Screen Test," The Japanese Journal of Clinical and Experimental Medicine, 2007, 84(8): 1152-1160 (with English language Abstract).
Da Rocha et al., "Cheating on College Examinations," 2007, Psychological Reports 2007, 100, 379-386, 8 pages.
David Heeger, "Signal Detection Theory", Psychology Department, NYU, Nov. 12, 1997, pp. 1-10, http://www.cns.nyu.edu/~david/handouts/sdt-advanced.pdf.
Fu et al., "Lying in the Name of the Collective Good: a Developmental Study," 2008, Developmental Science, 11(4):495-503, 9 pages.
Hara et al., "Estimating Overall Alzheimer's Disease Risk with Evidenced-Based Methods: Toward Prevention," The 10th International Conference on Alzheimer's Disease and Related Disorders, Poster Presentation, Madrid, Spain. Jul. 2006, pp. 1-7.
Harpp, et al, "Crime in the Classroom: Detection and prevention of cheating on multiple choice exams" 1993 [Online] Downloaded Nov. 26, 2012 http//pubs.acs.org/doi/abs/10.1021/ed070p306.
Kim, Tae Hoon, Authorized Officer, Korean Intellectual Property Office, International Search Report from related PCT Application No. PCT/US2011/043427, dated Feb. 9, 2012, 5 pages.
Kivipelto et al., "Risk Score for the prediction of dementia risk in 20 years among middle aged people: a longitudinal, population-based study," Lancet Neural. vol. 5, pp. 735-741.
Korean Intellectual Property Office, In International Search Report Application No. PCT/US2009/046169, dated Jan. 15, 2010, 11 pages.

Kwon, Youngkyong, Korean Intellectual Property Office, International Search Report for related PCT Application No. PCT/US2007/087656, dated Aug. 27, 2008, 10 pages.
Lippi et al., "New Strategies for Doping Control," Mar. 2008, Journal of Sports Sciences, 26(5):441-445, 5 pages.
McManus et al., "Learning in Practice," May 7, 2005, BMJ, vol. 330, 1064-1066, 3 pages.
Muhney, Kelly A. et al., The Prevalence of Academic Dishonesty in Texas Dental Hygiene Programs, Mar. 20, 2008, Journal of Dental Education, pp. 1247-1260, 14 pages.
Neurotrax_2003.pdf, p. 1-25.
Neurotrax_report.pdf, p. 1-9.
Ngandu et al., "The dementia Risk Score—A Practical Tool to Predict Dementia Risk in 20 Years Among Middle Aged Persons," The 10th International Conference on Alzheimer's Disease and Related Disorders, Poster Presentation, Madrid, Spain, Jul. 2006, 1 page.
Oda et al., "Does an Altruist-Detection Cognitive Mechanism Function Independently of a Cheater-Detection Cognitive Mechanism?", Mar. 27, 2006, Studies using Wason selection task, Evolution and Human Behavior, 366-380, 15 pages. (ISR).
Park, Mi Jeong, Authorized Officer, Korean Intellectual Property Office, PCT International Application No. PCT/US2009/037139, filed Mar. 13, 2009, in International Search Report, dated Oct. 27, 2009, 11 pages.
Pooley JP, Lee MD, Shankle WR. Modeling change in recognition bias with the progression of Alzheimer's. 2010, 6 pages.
Powrie et al., "Detection of Growth Hormone Abuse in Sport," 2007, ScienceDirect, 220-226, 7 pages.
Reisberg et al., "Staging Dementia", in Principles and Practice of Geriatric Psychiatry, Second Edition, edited by Copeland et al., Copyright 2002, John Wiley & Sons Ltd., pp. 142-145.
Reisberg, "Functional assessment staging (FAST)," Psychopharmacol Bull, 1988, 24(4): 653-9, Published by MedWorks Media Global, LLC, 1048 17th Street, Suite E, Santa Monica CA.
Rubin et al., "Children's Verbalizations and Cheating Behavior During Game Playing: The Role of Sociometric Status, Aggression, and Gender," Feb. 2003, Journal of Abnormal Child Psychology, 31(1):65-78, 14 pages.
Russano et al., "Investigating True and False Confessions Within a Novel Experimental Paradigm," 2005, American Psychological Society, 16(6):481-486, 6 pages.
Sclan et al., "Functional Assessment Staging (FAST0 n Alzheimer's Disease: Reliability, Validity, and Ordinality", International Psychogeriatrics, vol. 4, Supp. 1, 1992, pp. 55-69.
Shankle et al., "Relating Memory to Functional Performance in Normal Aging to Dementia Using Hierarchical Bayesian Cognitive Processing Models", Alzheimer Dis Assoc Disord, vol. 00, No. 00, Lippincott Williams & Wilkins, 2012, pp. 1-7.
Shankle et al., "Early Detection of Alzheimer's Disease and Related Disorders in Primary Care Practice," American Academy of Family Physician, Overview of Oral Presentation, San Francisco, CA, Oct. 2005, 2 pages.
Shankle et al., "Large Sample Analyses of AD and ADRD Risk Factors," Alzheimer's Association International Conference on Prevention of Dementia, Poster Presentation, Washington DC, Jun. 2007, 1-10.
Shankle et al., "Method to improve the detection of mild cognitive impairment", Mar. 2005, PNAS, vol. 102, No. 13, 4919-4924, 6 pages. (spec).
Shankle et al., "Toward Prevention of Alzheimer's Disease and Related Disorders: Risk Factor and Treatment Identification with Evidenced-Based Medicine," Alzheimer's Prevention Conference, Poster Presentation, Chicago, Illinois, Jun. 2005, 6 pages.
Shankle WR, Alva G, Lee MD. Bayesian cognitive models increase sensitivity for detecting treatment effect: Analysis of Flurizan phase 3 trial data. ICAD 2010. Poster Presentation, Jul. 2010, 1 page.
Shiffrin, et al., A Survey of Model Evaluation Approaches with a Tutorial on Hierarchical Bayesian Methods, Cognitive Science 32, 1248-1284 (2008).
Trenkle et al., "Detecting Cognitive Impairment in Primary Care: Performance Assessment of Three Screening Instruments," Journal of Alzheimer's Disease, 11(3): 323-335, 2007.

(56) References Cited

OTHER PUBLICATIONS

Weller et al., "Metric Scaling: Correspondence Analysis," Newbery Park, CA: SAGE Publications; pp. 1-95, 1990.
Unkel et al., "On the Procrustean analogue of individual differences scaling (INDSCAL)", Technical Report No. 144, Department of Statistics, University of Munich, http://www.stat.uni-muenchen.de, May 3, 2013, 32 pages.

\* cited by examiner

SYSTEMS AND METHODS FOR ASSESSING HUMAN COGNITION, INCLUDING A QUANTITATIVE APPROACH TO ASSESSING EXECUTIVE FUNCTION

CROSS-REFERENCE TO RELATED APPLICATIONS

This application is a U.S. national stage of International Application No. PCT/US2015/029883, filed May 8, 2015, which claims the benefit of priority of U.S. Patent Application No. 61/990,550, entitled "Systems and Methods for Assessing Human Cognition, Including a Quantitative Approach to Assessing Executive Function", filed May 8, 2014, which are incorporated herein by reference in their entirety.

BACKGROUND

This specification relates to assessing associative memory and judgment associated with a cognitive task, such as can be done based on results of a cognitive test that has been administered to a person.

Various techniques have been used to measure the cognitive function of a person. For example, the National Institute of Aging's Consortium to Establish a Registry of Alzheimer's Disease (CERAD) has developed a ten-word list as part of the Consortium's neuropsychological battery. The CERAD word list (CWL) test consists of three immediate-recall trials of a ten-word list, followed by an interference task lasting several minutes, and then a delayed-recall trial with or without a delayed-cued-recall trial. The CWL is usually scored by recording the number of words recalled in each of the four trials. A single cutoff score for the delayed-recall trial, with or without adjustment for demographic variables, is typically used to determine whether cognitive impairment exists for a given subject.

Some have proposed various improvements to the CWL. In addition, the CWL and the improvements thereof have been used to provide memory performance testing services, via the Internet, to clinicians in daily practice. Such services allow rapid testing of individual patients and reporting on the results of such testing. Previous reports for individual cognitive performance test results have included a statement of whether the patient has been found to be normal or to have cognitive impairment. Other reports have provided different result details, and other techniques for brain condition assessment have been described, which have included the use of triadic comparisons of items, (e.g., deciding which one of three animals is most different from the other two). For example, see U.S. Patent Pub. No. 2009-0313047, U.S. Patent Pub. No. 2009-0155754, and U.S. Patent Pub. No. 2013-0191153.

In addition, judgment is an executive function that involves attention, working memory, comparison, reasoning, and response selection. Executive function refers to a complex set of cognitive abilities used to perform tasks that involve one or more components of idea generation, reasoning, analysis, judgment, insight, synthesis of new ideas, decision making, planning, organization and execution. General brain processes are used to produce these executive functional abilities, and include attention, working memory, comparison (reasoning), response inhibition (eliminating irrelevant information), set-shifting (flexibility), development of new associations (discovery or concept formation), response selection or decision-making, task preparation, sequencing and execution. Judgment of semantic similarities or differences can be impaired by disorders disrupting inferior prefrontal cortex lobe function, including but not limited to Alzheimer's disease, Frontal temporal lobe disease, Lewy Body/Parkinson's disease, schizophrenia, multiple sclerosis, epilepsy, depression, and traumatic brain injury.

A variety of tests have been developed to measure components of executive function, including, but not limited to, the Stroop Color Interference test, the Wisconsin Card Sorting test, the Delis-Kaplan Frontal Systems battery, Symbol Digit Modalities Test, and many others. Because of the complex nature of executive function, the tasks that have been developed to measure it are also relatively complex to administer, interpret and score.

SUMMARY

This specification describes technologies relating to assessing associative memory and judgment associated with a cognitive task, plus methods of measuring judgment, so that the degree of impairment from normal aging to severe dementia can be quantified. In some implementations, a representational clustering measure is calculated from triadic comparison data.

In general, one or more aspects of the subject matter described in this specification can be embodied in one or more methods that include receiving data including a person's responses regarding judgments of semantic similarities between items selected from a group of items falling into a same categorical level, processing the data to determine a measure of distance within a generated representation of the person's responses regarding the judgments of semantic similarities, and generating a score of degree of cognitive impairment for the person based at least in part on the determined measure of distance within the generated representation. Other embodiments of this aspect include corresponding systems, apparatus, and computer program products.

For example, a system can include: a user device; and one or more computers, including hardware, programmed to interact with the user device and to perform operations of the method(s). The one or more computers can include a server system programmed to interact with the user device through a data communication network, and the user device can be programmed to interact with the server as a client. Alternatively, the user device can be a user interface device, the one or more computers can include the user interface device, and generating the score of degree of cognitive impairment can include outputting the score to a device including a non-transitory computer-readable medium.

These and other embodiments can optionally include one or more of the following features. The data can include delayed free recall responses of items presented for judgments of semantic similarities, and the responses regarding the judgments of semantic similarities can be responses to triadic comparisons. However, methods of comparisons other than triads can also be used. For example, paired comparisons can also be made and judgments of semantic similarities can be derived therefrom. In any case, generating a score of degree of cognitive impairment can include: determining the measure of distance within the generated representation using distance values calculated for the responses to the triadic comparisons within the generated representation; determining an additional measure for the delayed free recall responses using the calculated distance values for the responses to the triadic comparisons; and comparing the measure of distance with the additional measure to assess an interaction between judgment and associative memory when preparing the score.

The data for the triadic comparisons can include subject responses, response time per triad, items used for each triad, and their order of presentation per triad. The data for the delayed free recall can include items recalled, order of recall, response time per item recalled, repetitions and intrusions. The group of items falling into the same categorical level can be animals. For example, the animals can be antelope, beaver, camel, cat, chimpanzee, chipmunk, cow, deer, dog, elephant, giraffe, goat, gorilla, horse, lion, monkey, rabbit, rat, sheep, tiger, and zebra. Other animals can be used in various implementations. For example, if a free listing of animals by about ten subjects does not generate these twenty one animals as most common for a given culture, then culturally appropriate animals can be used. In any case, the animals (or other comparison items) selected from the group can be nine items selected from a group of twenty one items and be presented over twelve triadic comparisons.

Processing the data to determine a measure of distance can include: transforming the responses regarding the judgments of semantic similarities into a spatial representation; and applying a spatial randomness metric to the spatial representation. The transforming can include using a multidimensional scaling method applied to a proximity matrix generated for a subset of a group of people, where the proximity matrix indicates distances between each pair of the items of the group of items, and each of the distances are measured by how many times another item was selected as odd-one-out when presented with the corresponding pair.

The applying can include determining nearest-neighbor distances (i) within the spatial representation generated using the multidimensional scaling method and (ii) within generated configurations having points placed randomly within a multidimensional space created by the multidimensional scaling method. Further, the spatial randomness metric can include a ratio of observed mean nearest neighbor distance for the responses represented in the spatial representation to a mean nearest neighbor distance expected for random responses within the spatial representation, and the generating can include using (i) measured degrees of spatial randomness for responses of one or more groups of people to judgments of semantic similarities and (ii) delayed free recall responses by the one or more groups of people of items presented for judgments of semantic similarities.

Processing the data to determine a measure of distance can include: transforming the responses regarding the judgments of semantic similarities into a graph representation; and summing weighted edges within the graph representation to produce the measure of distance, where the weighted edges correspond to the person's responses regarding the judgments of semantic similarities. The generating can include comparing the measure of distance with sums of weighted edges for all possible response sequences associated with the judgments of semantic similarities between the items selected from the group. The generating can include comparing the measure of distance with sums of weighted edges for responses obtained from a sample of people. The weighted edges can be derived from a Standardized Weight Matrix (SWM) constructed from a number of populations, including populations with known cognitive deficits and age-matched sub-populations.

The generated representation can be derived from a generative Bayesian model for inferring a multidimensional scaling representation from individual-level trial-by-trial triadic comparison data. The Bayesian model can include a response determinism parameter that models individual differences in how a shared latent semantic structure generates decisions by measuring how closely an individual's choices adhere to the multidimensional scaling representation. In addition, the response determinism parameter can assign probabilities that vary exponentially with semantic similarities indicated by the multidimensional scaling representation, and the probabilities can be modeled to vary by individual between (i) full correspondence with the multidimensional scaling representation regarding the judgments of the semantic similarities and (ii) random responses that are uncorrelated with the semantic similarities.

Particular embodiments of the subject matter described in this specification can be implemented to realize one or more of the following advantages. A more quantitative approach to assessing, measuring and interpreting the executive function of judgment can be provided, which can be easier to administer and easier to perform than other existing executive function tests. According to an aspect of the described systems and techniques, judgment and associative memory tasks can be used that are minimally influenced by education and culture, are easy to administer, and are evaluated and interpreted with multidimensional scaling methods combined with measurement of spatial randomness. The results can be used to assess severity of cognitive impairment, from normal aging to severe dementia.

Triadic comparison and delayed free recall tasks data (e.g., for recall of animals) can be used to create an effective and differentiating representation of the effect of memory impairment on the structure of semantic representation. The representations can be used to reveal a successive decrease in semantic cluster structure and increase in uncertainty with increasing impairment. A measure of spatial organization can be used to quantify the visually evident changes in semantic organization, and demonstrate its usefulness for the different groups of subjects.

Moreover, individual differences in multidimensional scaling representations can be modelled based on inferring the extent to which each individual makes triadic comparisons consistent with a shared semantic representation, and these inferences can effectively reveal memory impairment even when the inferences are based on just 12 comparisons per subject. An approach to formalizing individual differences can include determining how deterministically the odd one out choices a person makes in triadic comparisons follow the inferred underlying semantic representation of the stimuli. The basic intuition is that this determinism provides a measure of the severity of impairment, with less impaired people closely following the choices predicted by the semantic structure, and more impaired people deviating from those predictions.

The details of one or more embodiments of the subject matter described in this specification are set forth in the accompanying drawings and the description below. Other features, aspects, and advantages of the invention will become apparent from the description, the drawings, and the claims.

DETAILED DESCRIPTION

Figure 1:
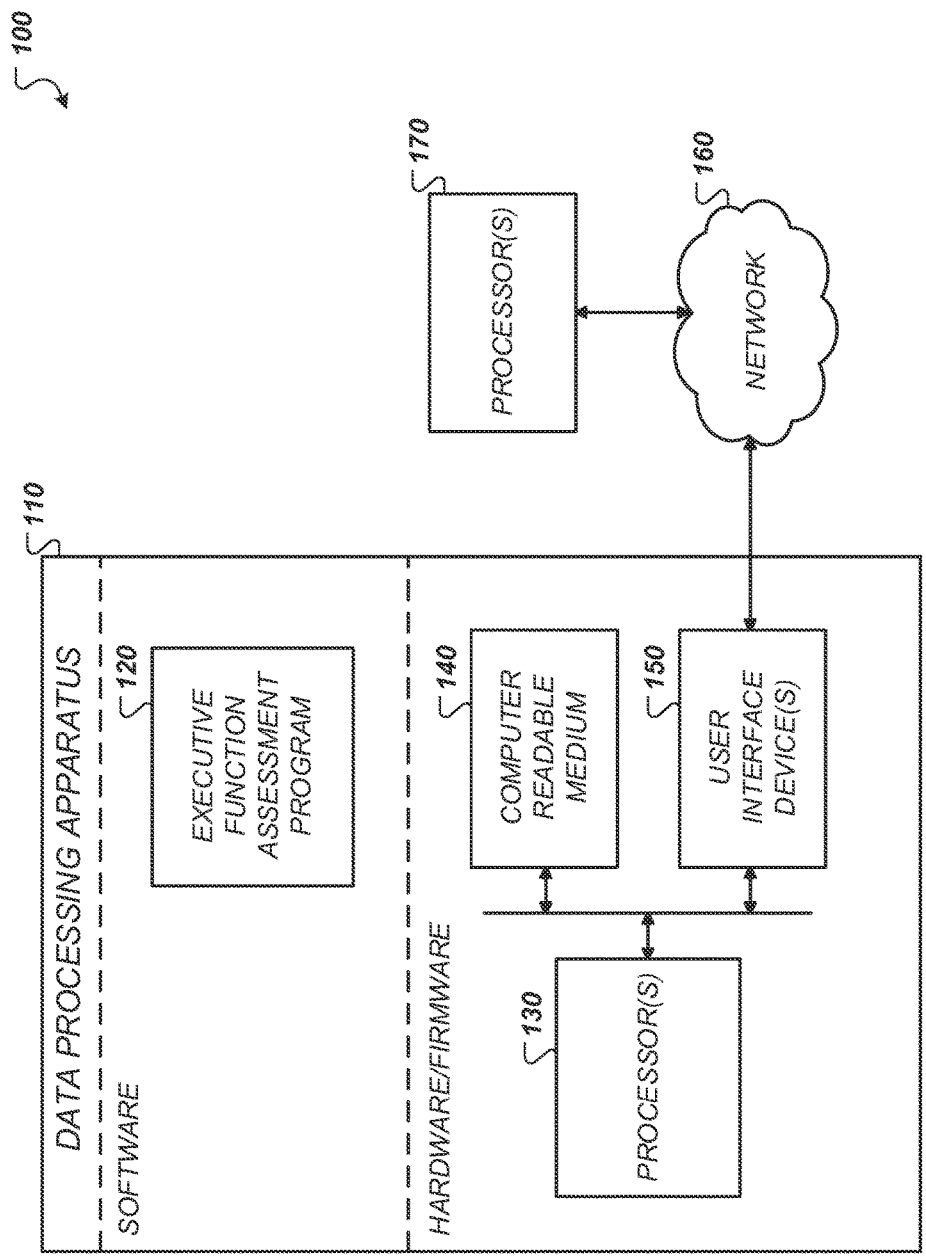
FIG. 1 shows an example of a system used to assess executive function.

FIG. 1 shows an example of a system 100 used to assess executive function. A data processing apparatus 110 can include hardware/firmware and one or more software programs, including an executive function assessment program 120. The executive function assessment program 120 operates in conjunction with the data processing apparatus 110 to effect various operations described in this specification. The program 120, in combination with the various hardware, firmware, and software components of the data processing apparatus, represent one or more structural components in the system, in which the algorithms described herein can be embodied.

The program 120 can be an application for determining and performing analysis on data collected to assess the executive function of a subject. A computer application refers to a computer program that the user perceives as a distinct computer tool used for a defined purpose. An application can be built entirely into an operating system or other operating environment, or it can have different components in different locations (e.g., a remote server). The program 120 can include or interface with other software such as database software, testing administration software, data analysis/computational software, and user interface software, to name a few examples. User interface software can operate over a network to interface with other processor(s). For example, the program 120 can include software methods for inputting and retrieving data associated with various recall tasks.

The program 120 can effect various analytic processes of recall task data, which processes are described further below. The data processing apparatus includes one or more processors 130 and at least one computer-readable medium 140 (e.g., random access memory, storage device, etc.). The data processing apparatus 110 can also include one or more user interface devices 150. User interface devices can include display screen(s), keyboard(s), a mouse, stylus, modems or other networking hardware/firmware, etc., or any combination thereof. The subject matter described in this specification can also be used in conjunction with other input/output devices, such as a printer or scanner. The user interface device can be used to connect to a network 160, and can furthermore connect to a processor or processors 170 via the network 160 (e.g., the Internet).

Therefore, a user of the assessment program 120 does not need to be local, and may be connecting using a web browser on a personal computer or a tablet computer, or using other suitable hardware and software at a remote location. For example, a clinician at a testing center can access a web interface via the remote processor 170 in order to input test data for a given test. The test data can be the results of an already administered test, or the test data can be the information exchanged when actually administering the test using a network based testing system. In any event, data can be transmitted over the network 160 to/from the data processing apparatus 110. Furthermore the clinician can input test data and retrieve analysis based on that data or other data stored in a database. Note that the data processing apparatus 110 can itself be considered a user interface device (e.g., when the program 120 is delivered by processor(s) 170 as a web service).

Figure 2:
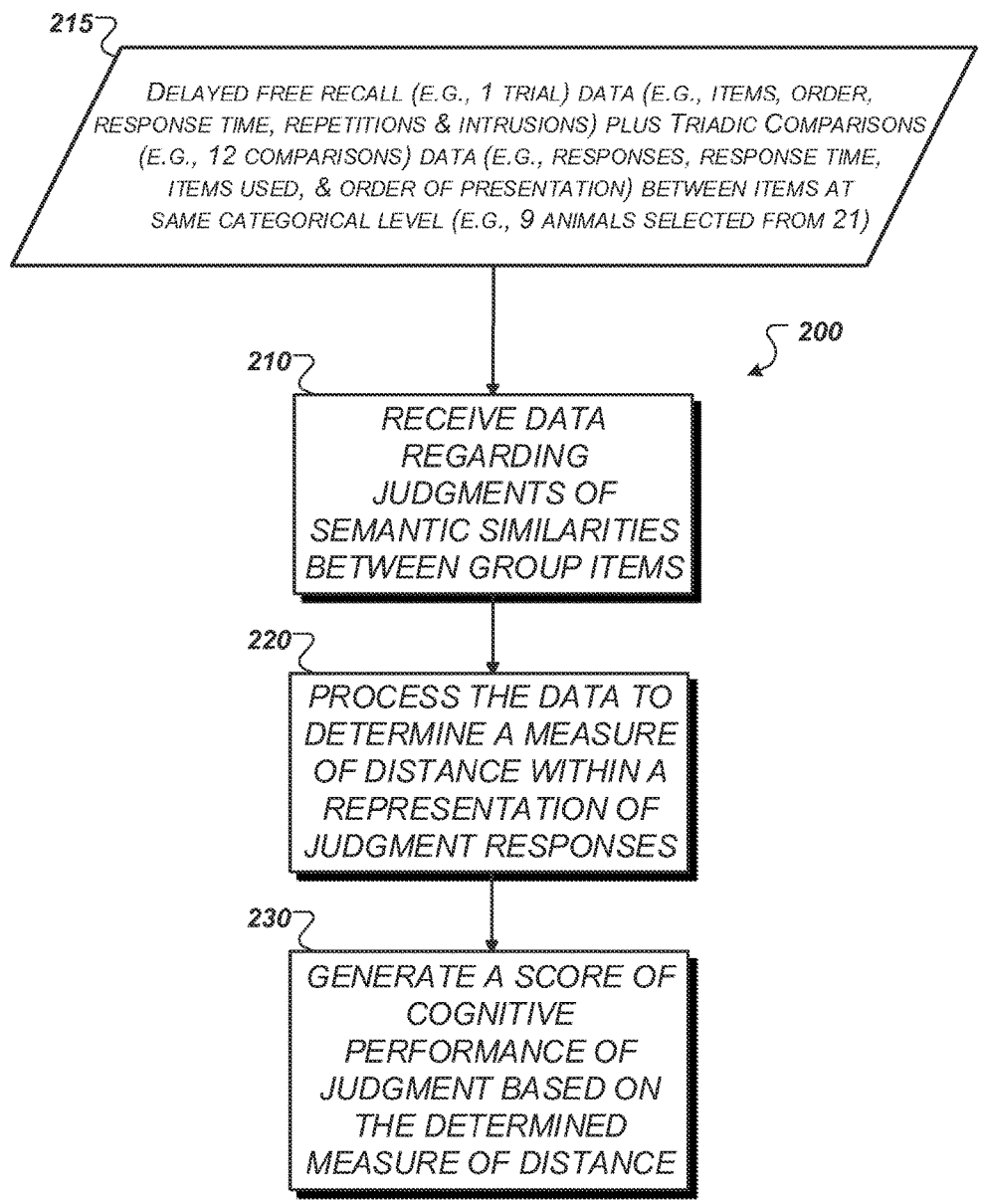
FIG. 2 shows an example of a process used to assess executive function.

FIG. 2 shows an example of a process 200 used to assess executive function. Data are received 210, where the data include a person's responses regarding judgments of semantic similarities between items selected from a group of items falling into a same categorical level. As noted above, the data can be from a previously administered test or from a test that is currently being administered. Nonetheless, the example process described in connection with FIG. 2, and other implementations of the more general concepts underlying this example process, are not practiced on the human body since such processes do not themselves involve an interaction necessitating the presence of the person.

The data can be received 210 from a database, a network or web-enabled device, a computer readable medium, or a standard input output device on a computer system, to name just a few examples. In some implementations, the task of triadic comparisons is used. Thus, the person's responses regarding the judgments of semantic similarities can be responses to triadic comparisons, and triadic comparisons data 215 can be received 210.

The triadic comparisons task has previously been used to study judgment of different sets of stimuli across a wide variety of cultures. Categories of stimuli studied include, but are not limited to, animals, kinships, colors, and emotions. The triadic comparisons task is largely free of cultural and educational influences, which can make it ideal for classification and longitudinal measurement. The triadic comparisons task is administered to subjects by presenting them verbally or visually with three stimuli, and asking them to select which stimulus is most different from the other two. The stimuli should be from the same categorical level, and not be superordinate or subordinate.

In some implementations, the group of items falling into the same categorical level for the data 215 is animals. For example, "dog" and "tiger" are from the same categorical level, whereas "animal" is superordinate to "rat", and "beagle" is subordinate to "dog". In order for each stimulus to be presented the same number of times as the other task stimuli, a balanced, lambda-1 design can be used. This balanced, lambda-1 design identifies the number of times a stimulus should be presented, and the number of triads needed to present each stimulus the same number of times. In some implementations the balanced, lambda-1 design results in nine animals being selected and presented over 12 triadic comparisons, such that each animal appears in four of the 12 triads.

This balanced exposure for each animal in the triadic comparisons task also facilitates measurement of delayed recall of the nine animals, which can be the last task performed in a screening test for cognitive impairment, and so the data 215 can also include delayed free recall data resulting from delayed free recall responses by the person of items presented for the judgments of semantic similarities. The delayed recall of the nine animals can facilitate simultaneous measurement of associative memory, mediated by association cortex and entorhinal cortex, plus judged similarities of the animals recalled, mediated by inferior prefrontal cortex. The order of the animals recalled should depend upon their judged similarity to each other. For example, during the triadic comparisons task, if "tiger" and "lion" are judged to be more similar than "tiger" and "sheep", and "tiger", "lion" and "sheep" are recalled during the delayed recall task, there is a higher probability that "tiger" and "lion" will be recalled closer to each other in the order of animals recalled, than will "tiger" and "sheep".

The triadic comparisons task can be constructed within a brief, online, cognitive assessment instrument, such as an online screening test for cognitive impairment, which can be administered by persons with brief training done online. To develop a list of animals for the triadic comparisons, subjects from five different regions (United States of America, United Kingdom, Japan, China, and Latin America) were instructed to name as many animals as they could think of within 90 seconds. The lists of animals generated by all subjects were compared, and the 21 most common animals listed across all five regions were selected as the candidate pool of animals. Thus, in some implementations, the candidate pool of animals includes: antelope, beaver, camel, cat, chimpanzee, chipmunk, cow, deer, dog, elephant, giraffe, goat, gorilla, horse, lion, monkey, rabbit, rat, sheep, tiger, and zebra. This animal pool can make the screening test more widely effective and the resulting data more useful.

Each time a subject is assessed with the triadic comparisons task, nine animals can be randomly selected from the pool of 21 animals, and 12 triads can be constructed using the lambda-1, balanced design previously described. Subject responses, response time per triad, the animals used for each triad, and their order of presentation can be recorded (e.g., into a database). At the end of the screening test, the subject can be asked to freely recall as many as they can, of the nine animals used in the triadic comparisons task. The animals recalled, order of recall, response time per animal recalled, and errors of intrusions or repetitions can also recorded (e.g., into the database). Repetitions are animals recalled more than once. Intrusions are animals or other words recalled that were not one of the nine animals of the triadic comparisons task. In other implementations, categories other than animals can be used, but the other aspects described (e.g., lambda-1, balanced design; recording for the triadic comparisons, subject responses, response time per triad, items used for each triad, and their order of presentation per triad; and recording for the delayed free recall, items recalled, order of recall, response time per item recalled, repetitions and intrusions) can still be used.

The received data is processed 220 to determine a measure of distance within a generated representation of the person's responses regarding the judgments of semantic similarities. In some implementations, this processing involves transforming the responses regarding the judgments of semantic similarities into a spatial representation, and applying a spatial randomness metric to the spatial representation. In some implementations, this processing involves transforming the responses regarding the judgments of semantic similarities into a graph representation, and summing weighted edges within the graph representation to produce the measure of distance, where the weighted edges correspond to the person's responses regarding the judgments of semantic similarities. Other approaches to determining a measure of distance within a generated representation are also possible.

In general, the representation is generated to facilitate assessment of subjects with different degrees of cognitive impairment, ranging from normal cognition to severe dementia. Detailed examples of generating such representations are described below for use in measuring task performance of a subject in making judgments of semantic similarities between items selected from a group, as described above, e.g., the constructed triadic comparisons task within the screening test.

Figure 3:
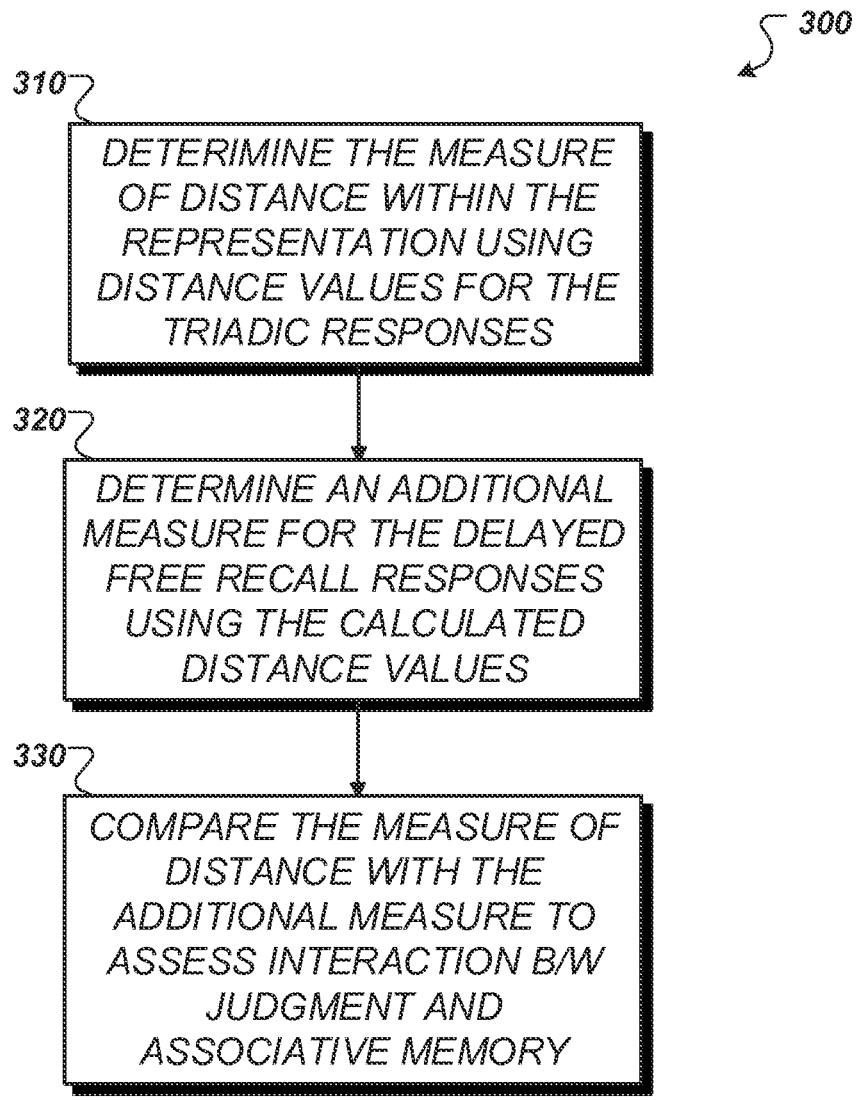
FIG. 3 shows an example of a process used to generate a score of degree of cognitive impairment for a person using a measure of interaction between a measure of associative memory and a measure of judgment.

A score of cognitive performance of judgment can be generated 230 for the person based at least in part on the determined measure of distance within the generated representation. This score represents a degree of cognitive impairment, which can range from normal cognition (no impairment) to severe dementia (significant impairment). FIG. 3 shows an example of a process 300 used to generate a score of degree of cognitive impairment for a person using a measure of interaction between a measure of associative memory and a measure of judgment. The measure of distance within the generated representation is determined 310 using distance values calculated for the responses to the triadic comparisons within the generated representation. An additional measure is determined 320 for the delayed free recall responses using the calculated distance values for the responses to the triadic comparisons. Finally, the measure of distance is compared 330 with the additional measure to assess an interaction between judgment and associative memory when preparing the score.

In some implementations, the basic features of the overall measurement method are: (1) collect a set of triadic comparisons over a range of subjects with differing degrees of cognitive impairment; (2) measure the similarity or dissimilarity of all pairs of the stimuli presented in the triads based on the odd-one-out choices in triadic comparison; (3) transform the similarity or dissimilarity measures into a spatial representation using multidimensional scaling methods; (4) apply a spatial randomness metric based on the distribution of nearest-neighbor distances to the spatial representation for a given subject/group's responses; (5) evaluate the relation between the degree of spatial randomness represented by a given subject or group's responses, and their degree of cognitive impairment; and (6) assign a score that measures the relation between degree of spatial randomness of the subject/group responses, and their degree of cognitive impairment.

A clinical sample of subjects with varying degrees of cognitive impairment were administered the online screening test as part of their initial assessment and follow-up visits, which usually occurred every three to six months. The data from the triadic comparisons of animals task were then analyzed after subdividing them into four groups with different levels of memory impairment, as described in further detail below. The four levels of memory impairment were defined by their delayed free recall of the nine animals used in the triadic comparisons task. The mean degrees of spatial randomness for these four memory impairment groups were computed as the observed/expected values, $$R = \overline{R}_{obs}/\overline{R}_{exp},$$

as described in further detail below.

Figure 4A:
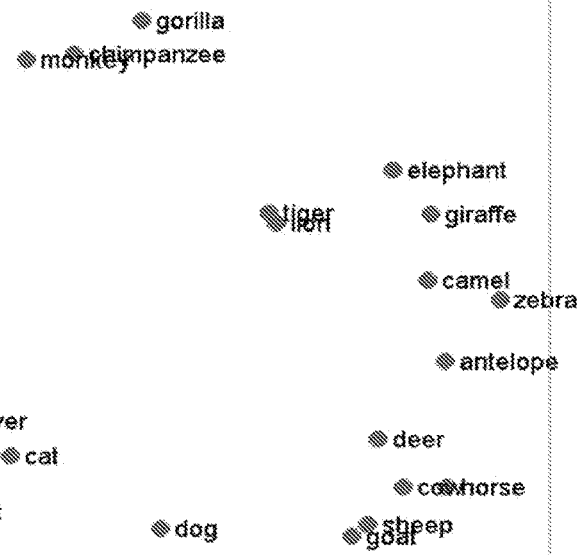
FIGS. 4A-4D show mean degree of spatial randomness for four memory impairment groups, plus two-dimensional spatial representations derived by multidimensional scaling from similarities.
Figure 4B:
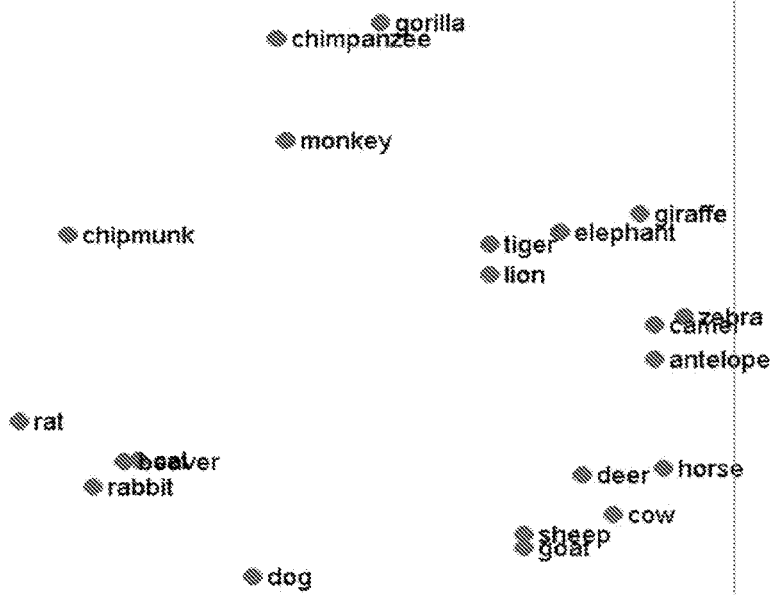
Figure 4C:
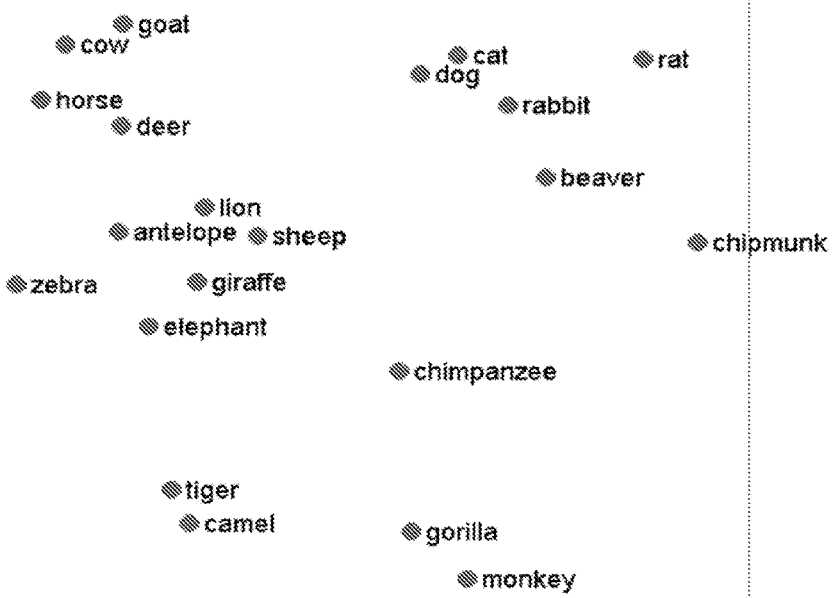
Figure 4D:
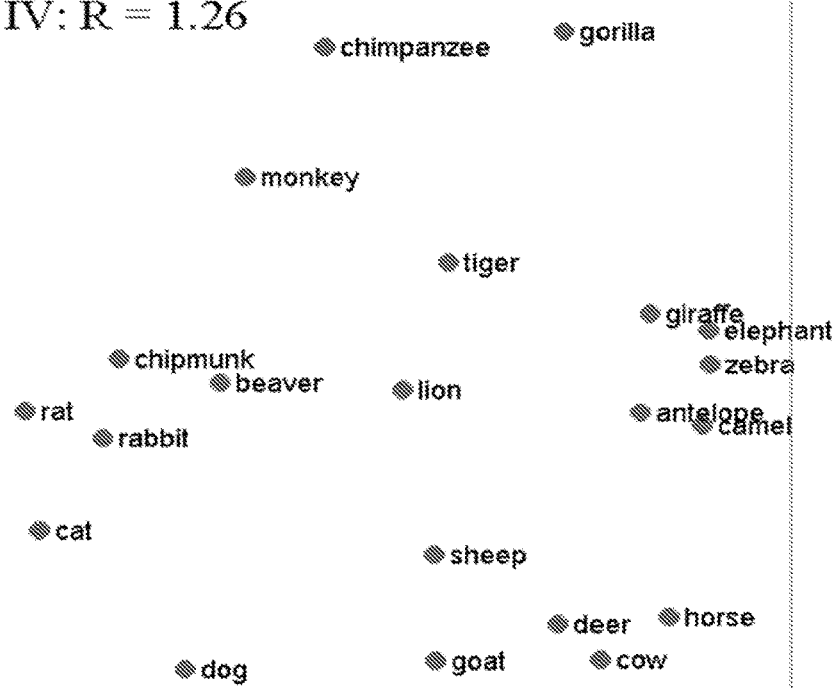

FIGS. 4A-4D show spatial representation of judged similarities for subjects at four different levels of memory impairment with the 2-dimensional spatial representations derived by multidimensional scaling from the similarities. R is the measure of spatial randomness of each plot. FIG. 4A shows the dimensional plot 400 for the group that recalled 9 out of 9 animals, with R=0.77. FIG. 4B shows the dimensional plot 410 for the group that recalled 7 or 8 out of 9 animals, with R=0.84. FIG. 4C shows the dimensional plot 420 for the group that recalled 4 to 6 out of 9 animals, with R=1.00. FIG. 4D shows the dimensional plot 430 for the group that recalled 0 to 3 out of 9 animals, with R=1.26.

The 2-dimensional similarity-based plots show greater separation between highly similar animals as memory declines. For example, the coordinates for monkey, chimpanzee and gorilla are almost identical for the "no memory impairment" group (FIG. 4A), but are widely separated for the severe memory impairment group (FIG. 4D). In terms of degree of spatial randomness, R, the two groups with the least memory impairment (FIGS. 4A, 4B) have the lowest values (0.77, 0.84), which indicate a greater degree of clustering in their similarity judgments than the two groups with the most memory impairment (FIGS. 4C, 4D: R=1.00, 1.26 respectively). These findings indicate that judgment can be quantified, and that it changes in a predictable manner with increasing severity of memory impairment.

Figure 5:
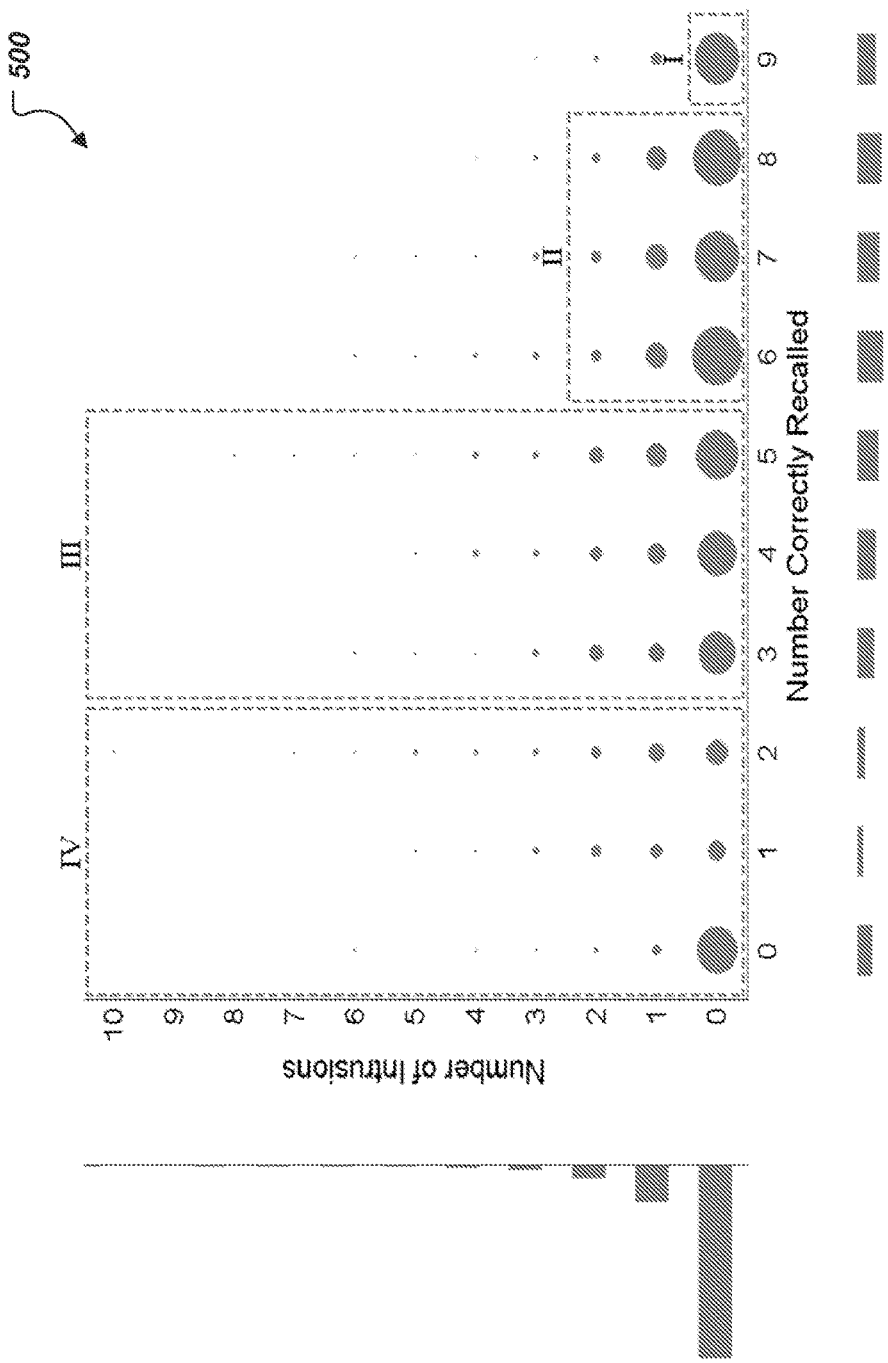
FIG. 5 shows a chart comparing the number of intrusions with the number of items correctly recalled during the associative memory delayed free recall task segregated in four groups.

FIG. 5 shows a chart 500 comparing the number of intrusions with the number of animals correctly recalled during the associative memory delayed free recall task segregated into four groups (I, II, III, IV). The sizes of the filled circles represents the proportions of subjects with the given number of intrusions, and the bars alongside the axes represent the marginal proportions of subjects for each number of intrusions or correctly recalled animals.

The number of animals correctly recalled represents the degree of encoding by association cortex and enthorhinal cortex into episodic memory (hippocampus). The number of intrusions represents words recalled that were not one of the nine animals used during the triadic comparisons task. When an intrusion is an animal not used during the triadic comparisons task, it represents a failure to distinguish between animals resident in long-term memory and animals resident in episodic memory (recently learned via associative encoding during the triadic comparisons task). When an intrusion is not an animal, it represents either forgetting the category of items used in the triadic comparisons task, or a failure to comprehend the delayed recall task instructions, or a semantic network failure when retrieving the class of animals.

Intrusions and correctly recalled animals use cognitive processes that differ from those used during the triadic comparisons task. The response data on intrusions and correctly recalled animals can therefore be used to classify subjects into four severity groups, which are then used to look for differences in the cognitive processes involved in performing the triadic comparisons task. In Group I (9 out of 9 animals correctly recalled), there are relatively fewer intrusions than in subjects who correctly recalled fewer than 9 animals. In Group II (6-8 animals correctly recalled), the proportion of subjects with zero or one intrusion is greater than for those who correctly recalled fewer than six animals. In Group III (3-5 animals correctly recalled), the proportion of subjects with zero or one intrusion is greater than for those who correctly recalled fewer than three animals. In Group IV (0-2 animals correctly recalled), the proportion of subjects with zero or one intrusion is less than for those who correctly recalled more than two animals.

As discussed in the previous paragraph, these groups represent an index of severity of cognitive impairment that is relatively independent of the cognitive processes involved in performing the triadic comparisons task. Performance of the triadic comparisons task can then be measured for each of the four groups and related to this cognitive severity index.

More than one approach can be used to measure judgment via the triadic comparisons task. In the following description of examples of such approaches, the data is denoted as follows. A total of I people complete a set of triadic comparisons involving a total of m stimuli. For their jth triad, the presented stimuli are $t_{ij1}$, $t_{ij2}$, and $t_{ij3}$. The data are the decisions, $y_{ij}$, made by the ith person on their jth triad, where $y_{ij}=t_{ij1}$ if $t_{ij1}$ was chosen, and so on.

For any subset of people, S, we calculate a proximity (distance) matrix between each pair of stimuli. For the wth and xth stimuli, the proximity measure is the proportion of times, for all the triads where both were included, that one of them was chosen as most different from the other two stimuli (i.e., odd-one-out). Intuitively, two stimuli become more similar every time the third one in the triad is chosen as the odd-one-out. So, treating proximity as the (additive) inverse of similarity (i.e. the shorter the proximity distance, the higher the similarity), two stimuli become more dissimilar every time one of them is chosen as the odd-one-out. Formally, denoting triads that include the wth and xth stimuli by $d_{wx}$, this definition can be written as:

$$d_{wx} = \frac{\sum_{i \in s} \sum_{j \in Twx} I(y_{ij} = t_{ijw} \vee y_{ij} = t_{ijx})}{\sum_{i \in s} \sum_{j \in Twx} 1}$$

where I (a) is the indicator function, taking the value 1 if the argument, a, is true, and 0 otherwise.

Figure 6:
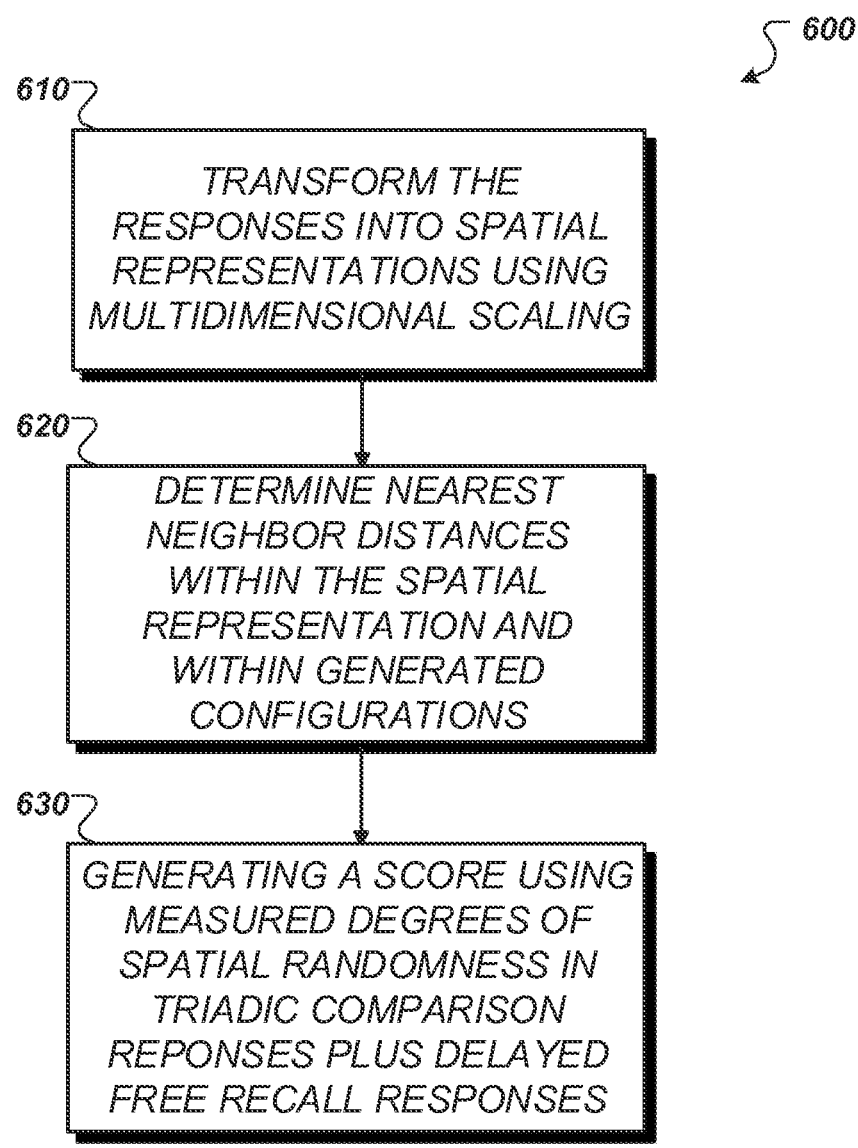
FIG. 6 shows an example of a process to determine a measure of distance within a generated spatial representation of a person's responses regarding judgments of semantic similarities and delayed free recall of the stimuli involved in the triadic comparisons task.

FIG. 6 shows an example of a process 600 to determine a measure of distance within a generated spatial representation of a person's responses regarding judgments of semantic similarities and delayed free recall of the stimuli involved in the triadic comparisons task. The responses regarding the judgments of semantic similarities can be transformed 610 into a spatial representation using a multidimensional scaling method applied to $D=(d_{wx})$. This can involve application of the classical multidimensional scaling algorithm as described by Borg & Groenen in 1997. Initially, $A=(a_{wx})$ can be calculated, where: $a_{wx}=-1/2\ d_{wx}$. Then $B=(b_{wx})$ can be calculated, where $b_{wx}=a_{wx}-a_{w\cdot}-a_{\cdot x}+a_{\cdot\cdot}$, and $a_{w\cdot}$ is a column sum of $(a_{wx})$, $a_{\cdot x}$ is a row sum of $(a_{wx})$, and $a_{\cdot\cdot}$ is the grand total.

The singular value decomposition, $B=U\lambda U'$, can then be taken, where U is the orthonormal matrix representation of B, and $\lambda$ is the singular value diagonal matrix of eigenvalues, which are the weights of each dimension of B. To spatially represent the stimuli, the coordinate locations, P, can be computed as $P=U\lambda^{1/2}$. The n dimensions associated with the greatest eigenvalues in $\lambda$ are retained. In some implementations, the classical multidimensional scaling procedure can be used to define a set of two-dimensional coordinate locations, $p_w=(p_{w1}, p_{w2})$ for the wth stimulus.

A spatial randomness metric can be applied to the spatial representation. In some implementations, nearest-neighbor distances can be determined 620 within the spatial representation generated using the multidimensional scaling method and also within generated configurations having points placed randomly within a multidimensional space created by the multidimensional scaling method. This can involve developing a clustering measure.

For example, the distances between multidimensional scaling representation points can be $$\hat{D} = (\hat{d}_{wx}), \text{ where } \hat{d}_{wx} = \left[\sum_{k=1}^{2}(p_{wk}-p_{xk})^2\right]^{\frac{1}{2}},$$

where k represents the two dimensions. The mean nearest neighbor distance in the multidimensional scaling representation can be calculated as:

$$\overline{R}_{obs} = \frac{1}{m}\sum_{w}\min_{w\ne x}\{\hat{d}_{wx}\},$$

where the minimization is calculated over the distances between the m stimuli, and w≠x. The expected mean nearest neighbor distance, $\overline{R}_{exp}$, can be calculated by generating many random configurations, then measuring the mean nearest neighbor distance of each configuration, and finally by computing the grand mean over all these configurations.

Each random configuration can be generated by independently placing m points in a square the same size as the multidimensional scaling representation, such that the probability of any point in the square being chosen is equal. Further, a score for the person can be generated 630 using measured degrees of spatial randomness for responses of one or more groups of people to judgments of semantic similarities and also using delayed free recall responses by the same one or more groups of people of the items presented for judgments of semantic similarities. As noted above, the levels of memory impairment can be defined by their delayed free recall of the selected items used in the triadic comparisons task. In addition, the final clustering measure can be the ratio of the observed to expected mean nearest neighbor distance, $R=\overline{R}_{obs}/\overline{R}_{exp}$, which is a measure of spatial randomness.

Figure 7:
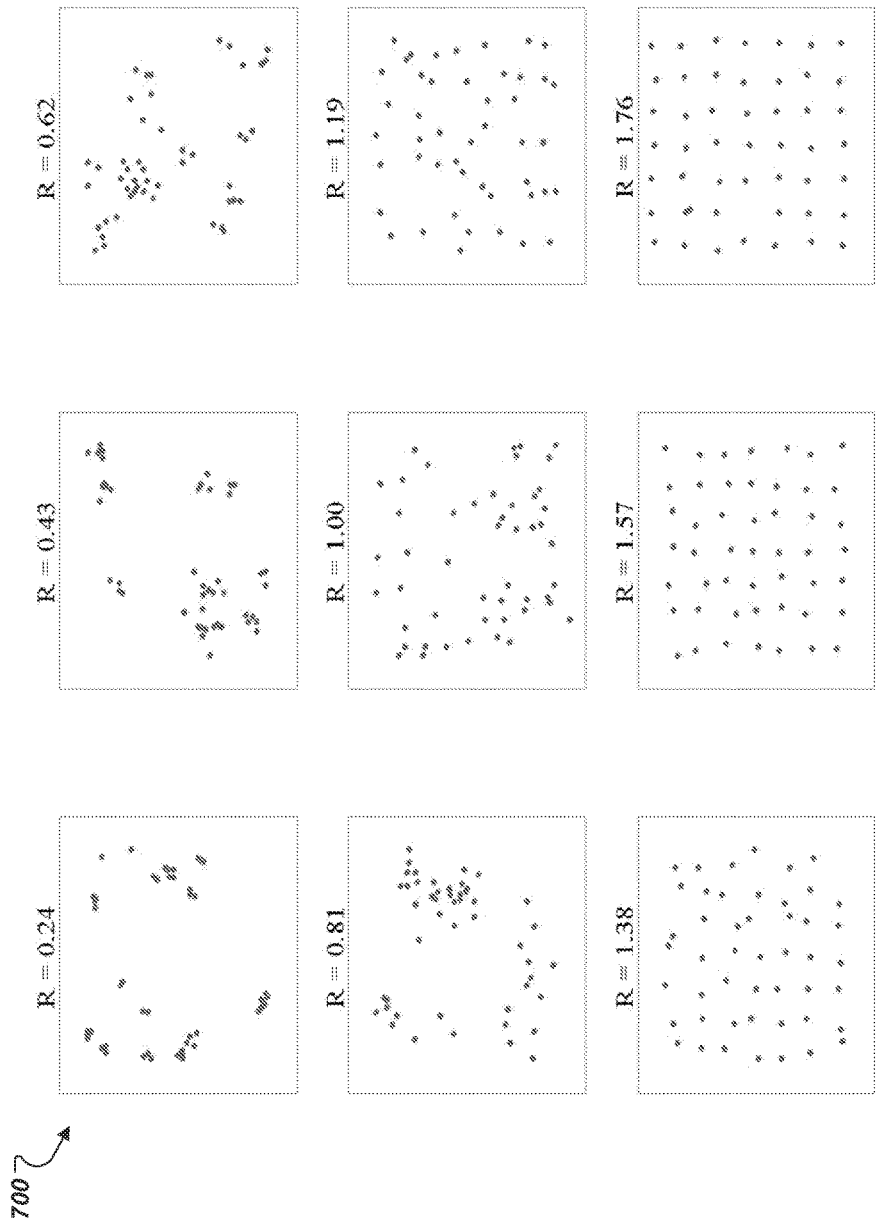
FIG. 7 shows plots, representing values of R, computed by the multidimensional scaling method, for different degrees of spatial clustering of a set of m points distributed in different arrangements within the same multidimensional space.

FIG. 7 shows plots 700, representing values of R, computed by the multidimensional scaling method, for different degrees of spatial clustering of a set of m points distributed in different arrangements within the same multidimensional space. These plots provide a reference frame for interpreting the results of the R values obtained from the triadic comparisons task for the four groups with different degrees of cognitive impairment. These plots show that the highly clustered points within a multidimensional space have R values of 0.24, 0.43, 0.62, and 0.81, whereas the plots with more randomly distributed points have R values of 1.00 and 1.19, and the plots with uniformly distributed points have R values of 1.38, 1.57, and 1.76.

The R values of plots 400, 410 in FIGS. 4A and 4B, created by the multidimensional scaling method applied to the triadic comparisons task data, are 0.77 and 0.84 for Groups I and II (no or minimal cognitive impairment), whereas the R values for plots 420, 430 in FIGS. 4C and 4D are 1.00 and 1.26 for Groups III and IV (more severe cognitive impairment). These R values from the triadic comparisons task increase with increasing cognitive impairment, and correspond to plots 700 in FIG. 7 that represent a relatively high degree of spatial clustering for Groups I and II, and a more random spatial representation for Groups III and IV. Intuitively, this can be interpreted to mean that less cognitively impaired subjects more correctly organize semantic similarities in the category of animals than do more cognitively impaired subjects.

Figure 8:
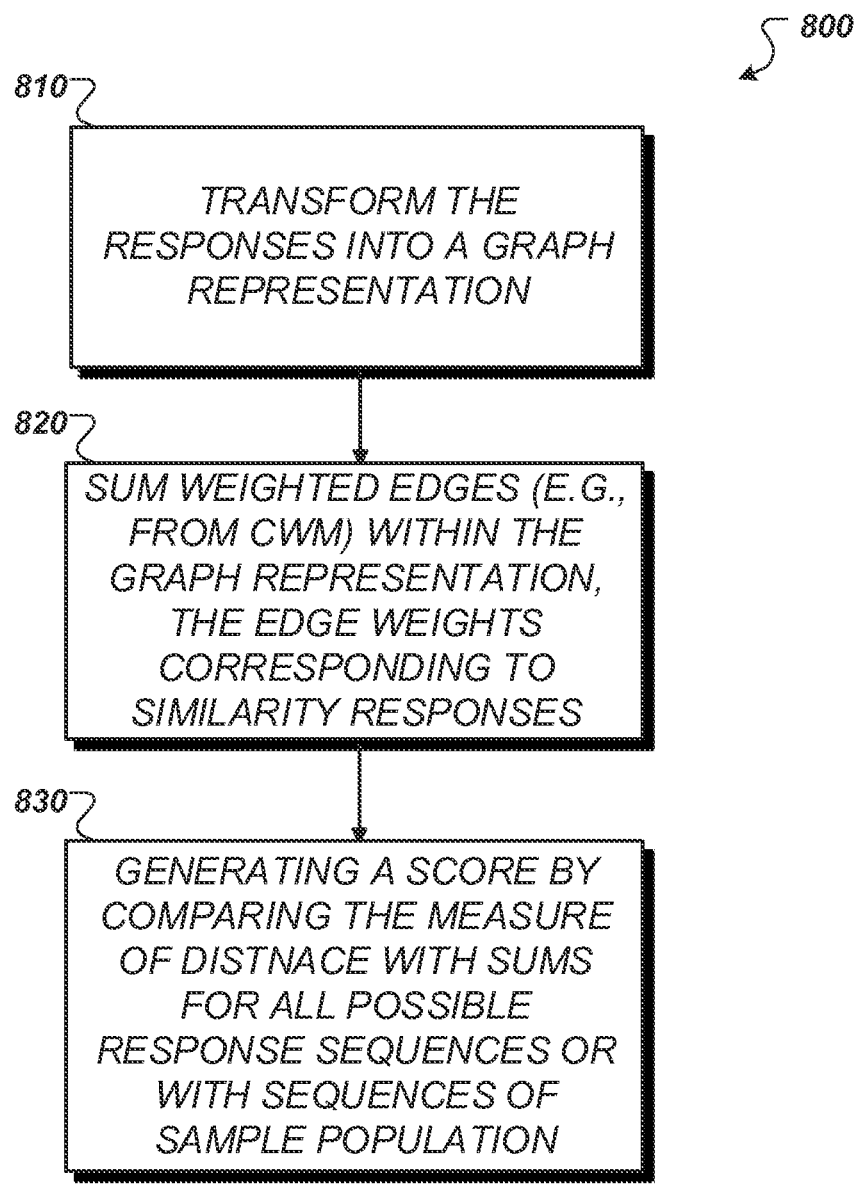
FIG. 8 shows another example of a process used to generate a score of cognitive performance for a person.

As noted above, more than one approach can be used to measure judgment via the triadic comparisons task. FIG. 8 shows another example of a process 800 used to generate a score of cognitive performance for a person. The responses regarding the judgments of semantic similarities can be transformed 810 into a graph representation, and weighted edges within the graph representation can be summed 820 to produce the measure of distance, where the weighted edges correspond to the person's responses regarding the judgments of semantic similarities. Thus, measuring judgment via the triadic comparisons task can involve using of a Sum of Weighted Edges (SWE) constructed from the subject's judgments and comparing it to a reference set of sums where the edge connecting two nodes in a graph are weighted. The weights can be derived from a normative sample, or other comparison sample, or theory.

When a subject selects an item in a triad, as most different from the other two items, the selected item is referred to as the "odd man out". If the triad consists of items {A, B, C}, the two items not selected as the odd man out represent the pair considered by the subject as most similar to each other among the three possible item pairs per triad ({A, B}, {A, C}, {B, C}). Over triadic comparisons of n triads, then n item pairs selected as most similar can be considered as edges connecting nodes in a graph. These edges are can be used to measure the subject's SWE of their judged triadic comparisons. This SWE can then be compared to all possible sums of n edges constructed from the same n triads, where each triad contributes one edge only to each sum. Thus, in some implementations, a score for the person can be generated 830 using the sums by comparing the measure of distance with sums of weighted edges for all possible response sequences associated with the judgments of semantic similarities between the items selected from the group.

A subject's SWE, or a group of subjects' SWEs, can be used to evaluate the cognitive impairment in judgment by comparing these sums to those obtained from the population of all possible sums derived from the same n triads, where each triad contributes one edge only to each sum. A subject with no cognitive impairment in judgment will generally have a shorter sum than the mean value derived from the population of all possible weighted sums with n edges. The SWEs of subjects with impaired judgment will generally differ from a sample of subjects with no impairment in judgment.

A subject's SWE, or a group of subjects' SWEs, can be used to evaluate for cognitive impairment in judgment by comparing these sums to those obtained from a normative sample of subjects. A subject with no cognitive impairment will have a shorter SWE derived from judged comparisons of n triads, because the item pairs selected will represent items that are semantically highly similar across a wide variety of cultures and educational levels. Comparison of a subject's SWE or a group of subjects' SWEs to those from a normative sample can therefore measure degree of normality of judgment.

The reference standard of SWEs that are compared to a subject's SWE or a group of subjects' SWEs can be constructed from a matrix of weighted edge lengths, called a Standardized Weight Matrix (SWM) 820, in which the weighting of the edges is standardized by the mean and standard deviation, e.g., of the set of items used to do the triadic comparisons task of any given subject at a given assessment. The SWM matrix can be obtained from other experiments and need not be restricted to the subjects involved in the triads test. One of the SWMs that can be used is from a set of cognitively normal college students. However, various sets of edge weights can be used from a number of populations to construct a SWM, including age-matched sub-populations or populations with known cognitive deficits. Additionally, the SWM edge weights need not be symmetric, such as occurs in confusion matrices, or even positive, such as occurs between items that are negatively associated.

For any given reference population, a SWM can be constructed for each unique set of items presented in the triadic comparisons task. The triadic judgments, in conjunction with the SWM, can be used to compute the population distribution (mean, $\overline{L}_{pj}$, and standard deviation, $\sigma_{pj}$) of all possible SWEs for the n triads in the task, using the same task items that the subject or subject group used, and using only one weighted edge per triad to construct the n weighted edges per sum. Since each subject or group of subjects may use different sets of items, indicated by the subscript j, the sum statistic can be normalized by the population standard deviation, $\sigma_{pj}$ so that comparisons are standardized by the subject population and by the set of items used to perform the triadic comparisons. This standardization permits a subject or group of subjects given the same set of items to be compared to the appropriate reference population for generation of the score.

Once a SWM's distribution parameters, $\overline{L}_{pj}$ and $\sigma_{pj}$, are computed, they can be used to evaluate the judged triadic comparisons of a subject or group of subjects by computing 830 their standardized score:

$$Z_{ij} = \left( \frac{L_{ij} - \overline{L}_{pj}}{\sigma_{pj}} \right)$$

where $Z_{ij}$ is the standardized SWE of subject, i, for item set, j, $L_{ij}$ is the observed SWE of subject, i, for item set, j, $\overline{L}_{pj}$ is the mean SWE of the reference population, p, for item set, j, and $\sigma_{pj}$ is the standard deviation of the SWE of the reference population, p, for item set, j, derived from the SWM The SWM. This methodology allows one to compare the judgment of a subject or a group of subjects in relation to a defined reference population, which is useful in assessing executive function in normal aging to severely demented subjects.

Note that different approaches can be used for calculation of the population mean and variance. For example, one approach is based directly on the triadic comparisons task and the appropriate SWM. Another approach is based on the delayed recall of those items and the appropriate SWM. These methodologies can be applied to the measurement of the judgment component of the delayed recall of animals as well. Using the spatial representation methodology, the value, R, can be computed for each adjacent pair of the recalled animals. For example, if two animals, w and x are recalled, one after the other, then one uses the value, $d_{wx}$, derived from the triadic comparisons task, to compute the value, R, for the delayed recall of animals task. This value of R can be compared to that derived from the triadic comparisons task, and may differ because of an interaction between judgment and associative memory.

Using the SWE methodology, the edge weights of each adjacently recalled pair of animals can be used to compute the SWE of a subject, or group of subjects, for the number of animals recalled. In an exactly analogous manner to the methodology described above, the subject's SWE can be compared to that of a reference population, in which the distribution of the reference population's SWE is derived using the same number of animals recalled as the subject or group of subjects, who had been tested with the same set of animals. This calculation then provides the $Z_{ij}$ score as previously described. Again, this $Z_{ij}$ score may differ from that derived from the triadic comparisons task because of an interaction between judgment and associative memory.

Returning to the multidimensional scaling approach addressed above, further improvements can be realized in representation of judgment. Bayesian methods can be used to infer multidimensional scaling (MDS) representation for each group (e.g., eight groups) based on their triadic comparisons (e.g., 12 triadic comparisons per subject). Reliable individual inferences can be based on the triadic comparisons data per subject, such as the animal triadic comparisons discussed above, which can provide a universally shared semantic representation.

The subject's choices are deterministic in the sense that they are determined by a universally shared semantic representation. However, the degree of memory impairment affects the subject's deterministic choices, and the degree to which a subject's deterministic semantic representation of recall items (e.g., animals) deviates from the universal representation varies systematically with the memory impairment group to which the subject belongs. This determinism provides a measure of the severity of impairment, with less impaired people closely following the choices predicted by the universally shared semantic structure, and more impaired people deviating from those predictions. This method differs from previous extensions of MDS to individual differences, such as the INDSCAL (INdividual Differences SCALing) model, which assumes individuals give different weights to different dimensions of a stimulus (e.g., noses on faces).

As described herein, a Bayesian approach for inferring MDS representations from individual-level trial-by-trial triadic comparison data can be used, where the Bayesian approach is based on graphical models and computational sampling methods. The Bayesian approach can have the advantage of characterizing the uncertainty of inferences about semantic representations. In addition, the distance measure can include an application of a measure of spatial randomness that is a statistical summary of the cluster structure in MDS representations, which quantifies change in semantic organization structure corresponding to changes in cognitive function by modeling individual differences in response determinism within a subject population. These individual differences can reveal the severity of impairment at the individual level.

Figure 9:
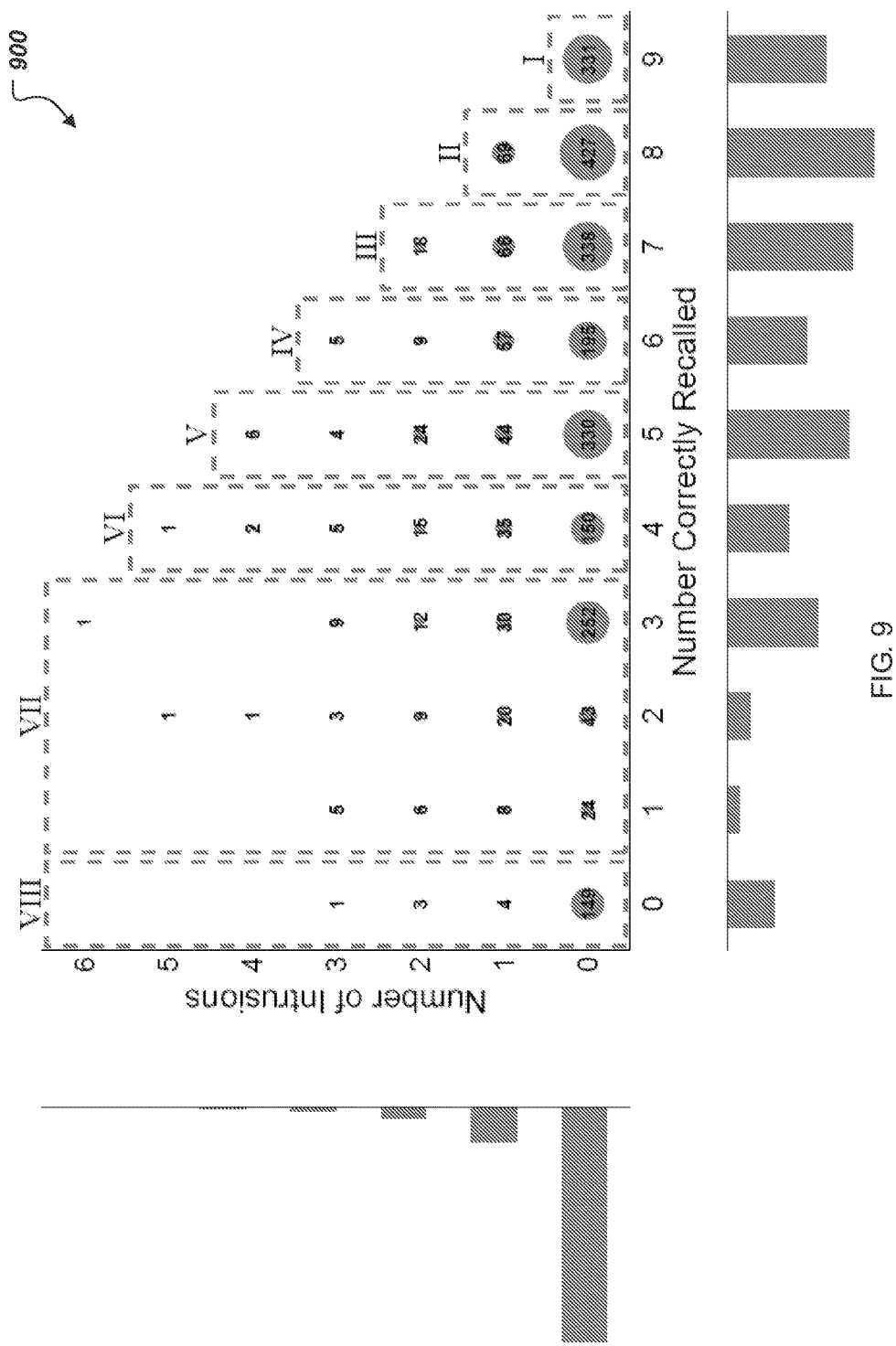
FIG. 9 shows a chart comparing the number of intrusions with the number of items correctly recalled during the delayed free recall task segregated in eight groups.

FIG. 9 shows a chart 900 comparing the number of intrusions with the number of items correctly recalled during the delayed free recall task, segregated in eight groups (I, II, III, IV, V, VI, VII, VIII). The data for the chart 900 comes from a cognitive disorders clinic and consists of 2,922 subjects ranging in severity from normal cognition to moderately severe dementia, who were cognitively assessed on 4,834 visits as part of the initial consultation plus routine follow up every three to six months. From this data set, the first visit of each of the 2,712 individual subjects is considered, and only their performance on tasks relating to the animals is used. These are the same animals discussed above, and the two tasks considered are the triadic comparisons of the animals (a subset of 9 selected from 21 animals) and the subsequent free recall of the animals. As before, the selection of animals for the twelve triadic comparisons can follow a lambda-1 design, which balances the pairings of the animals across the triads, so that each animal is presented in four triads. In the delayed free recall task, the patient is asked to recall as many of the nine animals as possible.

The sizes of the filled circles represent the proportions of subjects with the given number of intrusions, and the bars alongside the axes represent the marginal proportions of subjects for each number of intrusions or correctly recalled animals. The classification of the subjects into eight groups is based on measures of performance in the free recall of animals task. FIG. 9 summarizes patient performance on the delayed free recall task, and shows a method by which patients can be grouped for subsequent analyses. The main panel shows by the area of circles and labeled counts the joint distribution of the number of animals correctly recalled, between 0 and 9, and the number of intrusions recalled, between 0 and the observed maximum of 6.

Analysis of the data shows that the absolute level of difference in proportions from group I grows as impairment progresses from group II through to group VIII. In addition, the proportion of recall failures during the free recall task (i.e., differences in recall proportions) carries meaningful information for groups II through VII. Further, differences in the distribution of pairwise similarity values over all animal pairs also carry useful information. For example, groups corresponding to less impaired subjects skew with longer tails towards higher similarity values, whereas groups corresponding to greater impairment are more symmetric. For some groups, such as groups V, VI, and VIII, there is some suggestion of multimodality, with a set of very high pairwise similarities.

Figures 10, 11:
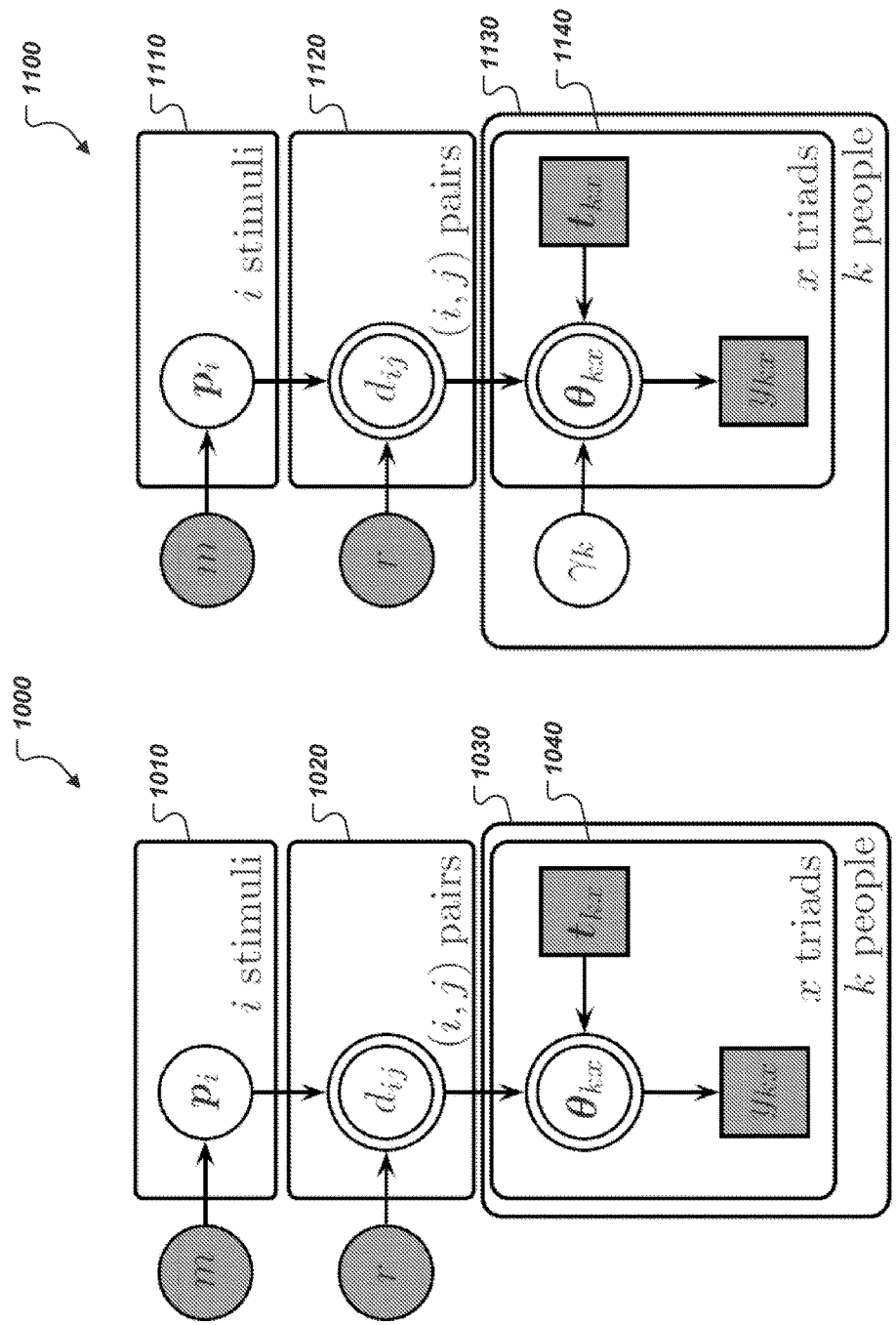
FIG. 10 shows a graphical representation of a generative model for inferring a spatial representation based on triadic comparisons.
FIG. 11 shows a graphical representation of another generative model for inferring a spatial representation based on triadic comparisons in which an individual response determinism parameter is included.

FIG. 10 shows a graphical representation 1000 of a generative model for inferring a spatial representation based on triadic comparisons. This graphical model is used to formalize the underlying assumptions about the MDS representational model and its relationship to the triadic comparison decisions, which is useful in explaining the probabilistic cognitive model being used.

The graphical representation 1000 quantifies the way in which latent model parameters generate observed behavioral data. Unshaded nodes represent unobserved parameters, shaded nodes represent observed data, and the graph structure indicates the dependencies between them. Other observed values, such as properties of the experimental design, are also shown as shaded nodes, and deterministic variables are shown as double-bordered nodes. Encompassing plates denote independent replications of the graph structure, iterating over participants, trials, or stimuli.

In this model, stimuli are represented as points in a multidimensional space, and the distances between them correspond to similarities that determine the choice probabilities in triadic comparisons. Thus, the latent coordinate locations $p_i=(p_{i1}, \ldots, p_{im})$ with $$p_i \sim \text{Uniform}(-10, 10)^m$$

represent the ith stimulus 1010 in an m-dimensional space and generate pairwise distances $d_{ij}$ 1020 with $$d_{ij} \leftarrow (\Sigma m' |p_{im'} - p_{jm'}|^r)^{1/r}$$

between the ith and jth stimuli according to the Minkowski r=metric. The three stimuli presented on the xth triad 1040 to the kth person 1030 are $t_{kx}=(t_{kx1}, t_{kx2}, t_{kx3})$.

An underlying presumption of the model is that the probability of choosing each of these three stimuli as the odd one out depends on the three pairwise distances between these stimuli. In particular, the probability of choosing $t_{kx1}$, represented by $\theta_{kx1}$, is proportional to the similarity between the other two stimuli, modeled as an exponential decay of the distance between them given by $\exp(-d_{t_{kx1},t_{kx2}})$. In addition, the generative model simply presumes that the chosen stimulus $y_{kx}$ is a categorical draw from the choice probabilities $\theta_{kx1}=1/Z(\theta_{kx1}, \theta_{kx2}, \theta_{kx3})$:

$$\theta_{kx} \leftarrow \frac{1}{Z}(\exp(-d_{t_{kx2},t_{kx3}}), \exp(-d_{t_{kx1},t_{kx3}}), \exp(-d_{t_{kx1},t_{kx2}}))$$

$$y_{kx} \sim \text{Categorical}(\theta_{kx})$$

Z is a normalizing constant to insure the probabilities sum to one. A key advantage of the graphical modeling approach is that it makes it practical to conduct fully Bayesian inference. Moreover, in some implementations, Markov-Chain Monte-Carlo methods can be used to return samples from the joint posterior distribution of the parameters conditional on the model and data.

To incorporate individual differences, it can be presumed that all subjects rely on the same, universal MDS representation of the animals in the task, but that memory impairment affects their ability to make triadic comparison choices consistent with this representation. The universality of the semantic representation of animal terms has a theoretical and empirical justification from a body of work in cultural anthropology that models culture as shared cognitive representations, and presents evidence for the constancy of MDS representations of animals, as well as color names and kinship terms. The individual differences in how this shared latent semantic representation generates decisions can be modeled using a version of the Luce-choice rule, in which the similarities between stimulus representations are affected by an individual-level, response determinism parameter.

Formally, the probability that the first stimulus will be chosen as the odd one out can be based on the exponentiated similarity of the other two stimuli, giving the choice probability:

$$\theta_1 = \frac{1}{Z}e^{(-d_{23})^\gamma} = \frac{1}{Z}e^{(-\gamma d_{23})}$$

where $\gamma$ is the positive response determinism parameter, and Z is a normalizing constant insuring the three choice probabilities sum to one.

FIG. 11 shows a graphical representation 1100 of another generative model for inferring a spatial representation based on triadic comparisons in which an individual response determinism parameter is included. The model is generally the same as that of FIG. 10, with the latent coordinate locations $p_i$ representing the ith stimulus 1110 in an m-dimensional space and generating pairwise distances $d_{ij}$ 1120 between the ith and jth stimuli according to the Minkowski r=metric. The three stimuli presented on the xth triad 1140 to the kth person 1130 are $t_{kx}=(t_{kx1}, t_{kx2}, t_{kx3})$, but in this case each person 1130 is modeled with the individual response determinism parameter $\gamma_k$.

In this model, the probability of choosing $t_{kx1}$, represented by $\theta_{kx1}$, is proportional to the similarity between the other two stimuli, modeled as an exponential decay of the distance between them given by $\exp(-d_{t_{kx1},t_{kx2}})$, but also includes the individual response determinism parameter $\gamma_k$:

$$\theta_{kx} \leftarrow \frac{1}{Z}(\exp(-\gamma_k d_{t_{kx2},t_{kx3}}), \exp(-\gamma_k d_{t_{kx1},t_{kx3}}), \exp(-\gamma_k d_{t_{kx1},t_{kx2}}))$$

Intuitively, the value of $\gamma$ controls how deterministically the responses based on the choice probabilities follow the underlying similarities. When $\gamma=1$, the Luce-choice rule reduces to the choice probabilities used in the generative model of FIG. 10. This corresponds to probability matching so that, for example, if the three pairwise similarities are 0.6, 0.3 and 0.1 then $\theta=(0.6; 0.3; 0.1)$.

In other words, the first stimulus will be chosen 60% of the time, the second 30%, and the third 10%. As $\gamma$ increases above 1, the largest similarity 0.6 will generate a relatively larger choice probability. For example, with $\gamma=2$ the choice probabilities become $\theta=(0.885; 0.111; 0.004)$, so that the first stimulus is now more likely to be chosen. In other words, as the determinism parameter increases, the stimulus that is least similar to the others according to the MDS representation becomes chosen as the odd-one-out with increasingly higher probability. In contrast, as $\gamma$ decreases below 1 towards 0, the probabilities move towards $\theta=(\frac{1}{3}; \frac{1}{3}; \frac{1}{3})$, regardless of the underlying similarities, and each stimulus becomes equally likely to be chosen as the odd-one-out. In this way, the determinism parameter spans a range from chance responding as $\gamma \to 0$, to probability matching at $\gamma=1$, to deterministic responding as $\gamma \to \infty$, and can be interpreted as measuring how closely an individual's choices adhere to an underlying MDS representation.

Thus, the generative model shown in the graphical representation 1100 infers a spatial representation based on triadic comparisons, but also incorporates individual-level differences in the determinism of comparisons. The MDS representation of the graphical representation 1100 for the individual-level analysis, using the Luce-choice rule approach, still has the ith stimuli 1110 represented by the coordinate location pi in an m-dimensional, generating pairwise distances $d_{ij}$ 1120 under the Minkowski r=metric. For the kth person 1130, these distances generate choice probabilities for the xth triad 1140, $\theta_{kx}$ according to their determinism, $\gamma_k$, which is given a Gamma(2,1) prior. This prior was chosen so that the model is at the special case, $\gamma=1$, of probability matching, but larger and smaller values are given significant prior density. As in the original model, the behavioral data are categorically distributed according to the choice probabilities.

Figure 12A:
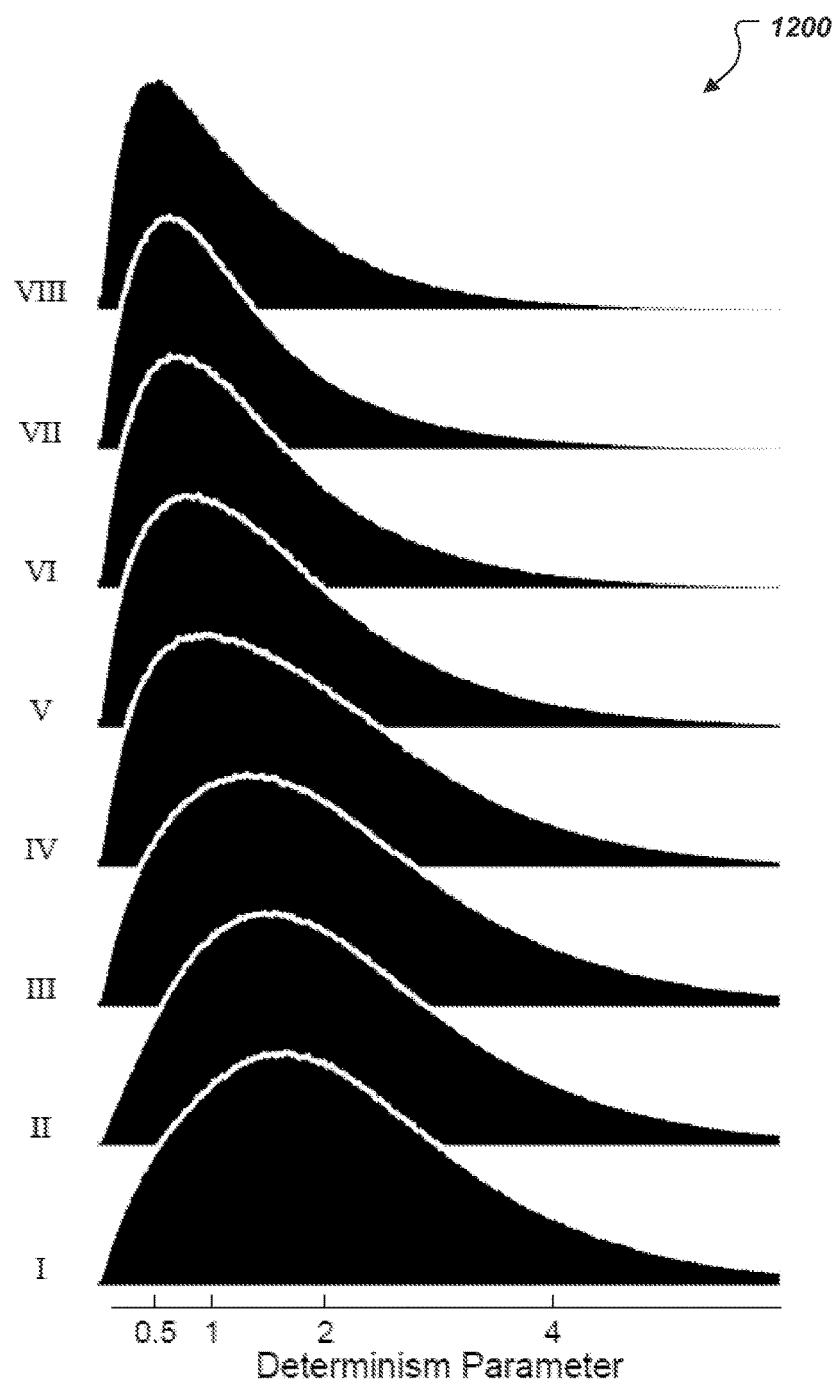
FIGS. 12A-12B show resulting inferred determinism parameter values for groups and individuals.
Figure 12B:
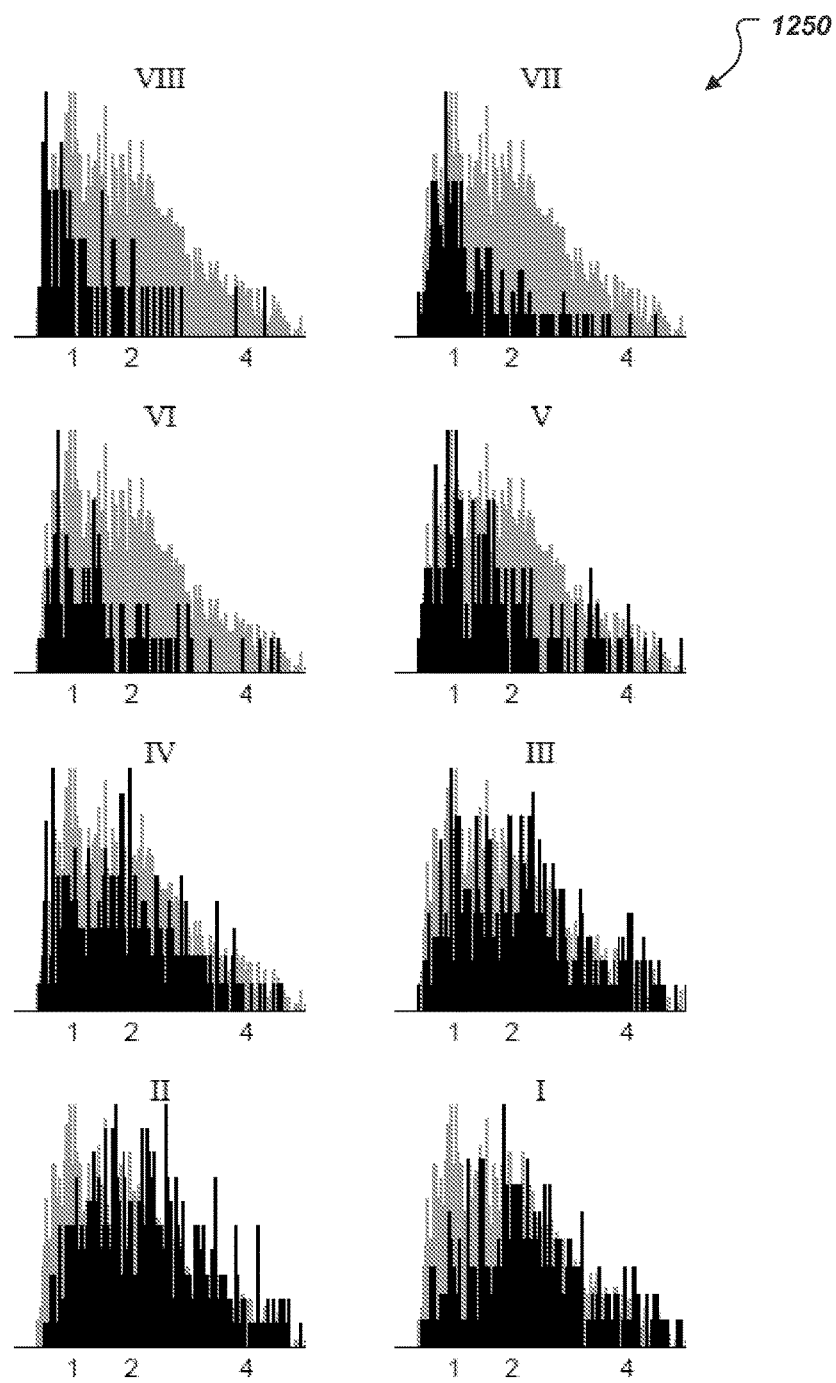

Applying the model of FIG. 11 to the first visit data for all 2,162 subjects described above provided results based on 3 independent chains each containing 5000 samples, collected after 5000 discarded burn-in samples. The chains were again checked visually and with the $\hat{R}$ statistic for convergence. FIGS. 12A-12B show the resulting inferred determinism parameter values for groups and individuals.

FIG. 12A shows the posterior uncertainty 1200 for groups I to VIII. FIG. 12B show the distribution (in black) of the posterior expectation for each individual in groups I to VIII, referenced against the distribution (in gray) for all individuals in all groups 1250. It is clear that the distribution of these individual-level measures shift from larger to smaller values as severity increases. The posterior expectations of the determinism parameter do not clearly separate individual patients into different severity groups, but instead show considerable overlap. This is not surprising, since the analysis at an individual level is based on just 12 triadic comparison choices involving only 9 of the 21 animal stimuli. It is possible the information latent in these data is not sufficient for confident and accurate measures of a patient's severity of impairment under any analysis. What the current results show through the clear trends in the individual estimates is that the approach to modeling individual differences developed here is potentially useful, because it captures useful information about severity at the level of specific patients on specific testing occasions.

FIGS. 12A-12B present the main results, focusing on the determinism parameter, $\gamma$. FIG. 12A shows the posterior distribution over the $\gamma$ parameter for all those patients in each severity group. That is, it combines the posterior samples for every patient in each group, to form an overall distribution. The group membership information is not available to the model, so this analysis is best interpreted as testing whether the determinism parameter approach to individual differences is able to measure differences in the severity of impairment of the groups. While the posterior distributions in FIG. 12A overlap significantly, they do progress from larger to smaller values as severity increases from group I to group VIII. The values $\gamma$ takes are also interpretable. Among subjects in the least impaired groups, the densities of their $\gamma$ parameters are mostly above 1, which corresponds to their more deterministic judgments. Among subjects in the most impaired groups, the densities of their $\gamma$ parameters are mostly below 1, which corresponds to their more random judgments of animals.

The smaller panels in FIG. 12B present a more applied analysis of the individual differences model. Each panel corresponds to the subjects in one of the severity groups, showing the distribution of the posterior expectation of their $\gamma$ parameter. This means that, in these analyses, each person's response determinism is summarized by a point estimate, and the distribution of these point estimates over all the patients in the group is shown in black. In all of the panels, the entire distribution of these point summaries for all patients is shown in gray, to allow visual comparison. Thus, as shown, MDS models based on triadic comparisons (e.g., of animals) can be used to measure judgments of individual subjects and relate them to severity of impairment.

Moreover, unlike previous work that have often assumed that individual differences can be understood in terms of different people attending to the dimensions of the stimuli in different ways, which is a sort of selective attention mechanism that can be successfully and intuitively used to model cognitive phenomena like category learning but also seems most applicable when there are clear and separable underlying dimensions that characterize the stimuli, the MDS representations describe herein need only be two-dimensional and rely on a Euclidean distance metric, which theoretically corresponds to integral rather than separable stimuli. Rather than consider higher-dimensional representations with a city-block metric, which could be accomplished in the Bayesian framework by changing m and r in the graphical models, a different approach can be taken to account for individual differences. Specifically, it can be presumed that there is a shared or universal MDS representation of the items in the group (e.g., the animal names), but different people make dis-similarity judgments that vary in degree with this representation. Formalizing this presumption has resulted in a new model in which individual differences are parameterized in terms of response determinism, which can be conceived as a measure of how consistently an individual makes the choices predicted by the underlying representation.

The application of this model to a dataset showed that, even though each individual made only 12 decisions about a subset of the stimuli (9 of 21 animals), the determinism parameter permitted useful inferences about memory impairment at the individual level. Overall, the MDS representation models and decision-making models of judged comparisons, as described herein, identified a relationship between semantic clustering and memory impairment that was not evident from standard analyses of the same data. Given that these are clinical practice data, and that the 12 triads assessed per subject was small enough to be doable even in primary care settings, the results of both group and individual analyses are even more impressive, and support the potential for model-based clinical data analysis.

Further testing of the relationship between semantic organization and memory impairment can be achieved by considering independent assessments of the severity of impairment for patients, such as Functional Assessment Staging Test (FAST) staging classifications. Further refinements of the model can be achieved by using different underlying assumptions including different representational models and cognitive processes for relating stimulus similarity to choice behavior. Given the demonstrated promise of the models, measures, and methods developed, and the rich possibilities for further investigation, the described joint reliance on cognitive models and Bayesian methods can become a standard approach in study of the effect of memory impairment on semantic representation.

Figure 13:
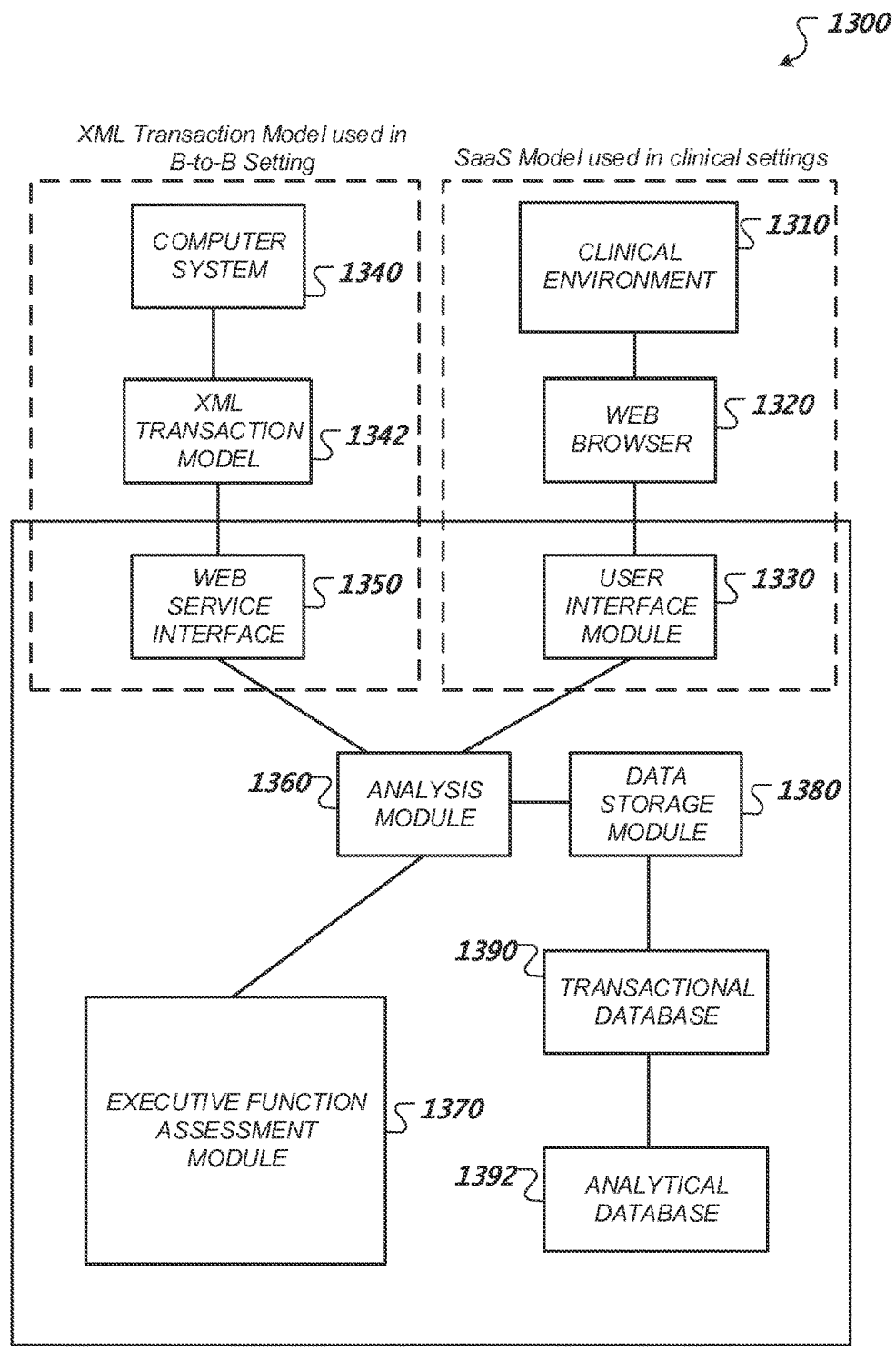
FIG. 13 shows another example of a system used to assess executive function.

As will be appreciated, various computer systems can be used to implement the systems and techniques described herein and perform computational analysis using cognitive models and Bayesian methods, as described, to assess executive function based on responses to a test involving judgments of semantic similarities. For example, FIG. 13 shows another example of a system 1300 used to assess executive function. The example system described can perform a variety of functions including data analysis, storage and viewing, and remote access and storage capabilities useful for generating and using the analysis techniques described herein.

A Software as a Service (SaaS) model can provide network based access to the software used to generate the analysis. This central management of the software can provide advantages, which are well known in the art, such as offloading maintenance and disaster recovery to the provider. A user, for example, a test administrator within a clinical environment 1310, can access test administration software within the test administration system via a web browser 1320. A user interface module 1330 receives and responds to the test administrator interaction.

In addition, a customer's computer system 1340 can access software and interact with the test administration system using an eXtensible Markup Language (XML) transactional model 1342. The XML framework provides a method for two parties to send and receive information using a standards-based, but extensible, data communication model. A web service interface 1350 receives and responds to the customer computer system 1340 in XML format. For example, an XML transactional model can be useful for storage and retrieval of the structured data relating to the model(s) of cognitive processes (e.g., Bayesian models) and the item response data.

An analysis module 1360 analyses inputs from the web service interface 1350 and the user interface module 1330, and produces test results to send. The analysis module uses an executive function assessment module 1370 to perform the test analysis using the model(s), as described herein. The executive function assessment module 1370 can, for example, incorporate a generative model that includes a Bayesian model for inferring a multidimensional scaling representation from individual-level trial-by-trial triadic comparison data as described above in this specification.

A data storage module 1380 transforms the test data collected by the user interface module 1330, web service interface 1350, and the resulting data generated by the analysis module 1360 for permanent storage. A transactional database 1390 stores data transformed and generated by the data storage module 1380. For example, the transactional database can keep track of individual writes to a database, leaving a record of transactions and providing the ability to roll back the database to a previous version in the event of an error condition. An analytical database 1392 can store data transformed and generated by the data storage module 1380 for data mining and analytical purposes.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a cross-platform runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims.

What is claimed is:

1. A computer-implemented method comprising:
   receiving data comprising (i) a person's responses regarding judgments of semantic similarities between items selected from a group of items falling into a same categorical level, and (ii) delayed free recall responses by the person of items presented for the judgments of semantic similarities, wherein the responses regarding the judgments of semantic similarities are responses to triadic comparisons;
   processing the data to determine a measure of distance within a generated representation of the person's responses regarding the judgments of semantic similarities, wherein the processing comprises transforming the responses regarding the judgments of semantic similarities into a spatial representation and applying a spatial randomness metric to the spatial representation, and wherein the spatial randomness metric comprises a ratio of observed mean nearest neighbor distance for the responses represented in the spatial representation to a mean nearest neighbor distance expected for random responses within the spatial representation; and
   generating a quantitative score of executive function for the person based at least in part on the determined measure of distance within the generated representation regarding the judgments of semantic similarities, and providing the quantitative score of executive function, to a user device of a human cognition assessment system comprising one or more computers, for use by a clinician in assessing cognitive impairment of the person, wherein the generating comprises:
   determining the measure of distance within the generated representation using distance values calculated for the responses to the triadic comparisons within the generated representation;
   determining an additional measure for the delayed free recall responses using the calculated distance values for the responses to the triadic comparisons; and
   comparing the measure of distance with the additional measure to assess an interaction between judgment and associative memory when preparing the score; and
   wherein the generating comprises using (i) measured degrees of spatial randomness for responses of one or more groups of people to judgments of semantic similarities and (ii) delayed free recall responses by the one or more groups of people of items presented for judgments of semantic similarities.

2. The method of claim 1, wherein the data comprises:
   for the triadic comparisons, subject responses, response time per triad, items used for each triad, and their order of presentation per triad; and
   for the delayed free recall, items recalled, order of recall, response time per item recalled, repetitions and intrusions.

3. The method of claim 1, wherein the group of items falling into the same categorical level is animals.

4. The method of claim 3, wherein the animals are antelope, beaver, camel, cat, chimpanzee, chipmunk, cow, deer, dog, elephant, giraffe, goat, gorilla, horse, lion, monkey, rabbit, rat, sheep, tiger, and zebra.

5. The method of claim 3, wherein the animals selected from the group are nine animals selected from a group of twenty one animals and presented over twelve triadic comparisons.

6. The method of claim 1, wherein the transforming comprises using a multidimensional scaling method applied to a proximity matrix generated for a subset of a group of people, wherein the proximity matrix indicates distances between each pair of the items of the group of items, and each of the distances are measured by how many times another item was selected as odd-one-out when presented with the corresponding pair.

7. The method of claim 6, wherein the applying comprises determining nearest-neighbor distances (i) within the spatial representation generated using the multidimensional scaling method and (ii) within generated configurations having points placed randomly within a multidimensional space associated with the multidimensional scaling method.

8. The method of claim 1, wherein the processing comprises:
transforming the responses regarding the judgments of semantic similarities into a graph representation; and
summing weighted edges within the graph representation to produce the measure of distance, wherein the weighted edges correspond to the person's responses regarding the judgments of semantic similarities.

9. The method of claim 8, wherein the generating comprises comparing the measure of distance with sums of weighted edges for all possible response sequences associated with the judgments of semantic similarities between the items selected from the group.

10. The method of claim 8, wherein the generating comprises comparing the measure of distance with sums of weighted edges for responses obtained from a sample of people.

11. The method of claim 10, wherein the weighted edges are derived from a Standardized Weight Matrix (SWM) constructed from a number of populations, including populations with known cognitive deficits and age-matched subpopulations.

12. The method of claim 1, wherein the generated representation is derived from a generative Bayesian model for inferring a multidimensional scaling representation from individual-level trial-by-trial triadic comparison data.

13. The method of claim 12, wherein the Bayesian model includes a response determinism parameter that models individual differences in how a shared latent semantic structure generates decisions by measuring how closely an individual's choices adhere to the multidimensional scaling representation.

14. The method of claim 13, wherein the response determinism parameter assigns probabilities that vary exponentially with semantic similarities indicated by the multidimensional scaling representation, and wherein the probabilities are modeled to vary by individual between (i) full correspondence with the multidimensional scaling representation regarding the judgments of the semantic similarities and (ii) random responses that are uncorrelated with the semantic similarities.

15. A computer-readable medium encoding a computer program product operable to cause data processing apparatus to perform operations comprising:
receiving data comprising a person's responses regarding judgments of semantic similarities between items selected from a group of items falling into a same categorical level, the responses regarding the judgments of semantic similarities comprising responses to triadic comparisons;
processing the data to determine a measure of distance within a generated representation of the person's responses regarding the judgments of semantic similarities, wherein the generated representation is derived from a generative Bayesian model for inferring a multidimensional scaling representation from individual-level trial-by-trial triadic comparison data, and wherein the Bayesian model includes a response determinism parameter that models individual differences in how a shared latent semantic structure generates decisions by measuring how closely an individual's choices adhere to the multidimensional scaling representation, wherein the processing comprises transforming the responses regarding the judgments of semantic similarities into a spatial representation and applying a spatial randomness metric to the spatial representation, and wherein the spatial randomness metric comprises a ratio of observed mean nearest neighbor distance for the responses represented in the spatial representation to a mean nearest neighbor distance expected for random responses within the spatial representation; and
generating a quantitative score of executive function for the person based at least in part on the determined measure of distance within the generated representation regarding the judgments of semantic similarities, wherein the generating comprises using (i) measured degrees of spatial randomness for responses of one or more groups of people to judgments of semantic similarities and (ii) delayed free recall responses by the one or more groups of people of items presented for judgments of semantic similarities, and providing the quantitative score of executive function, to a user device of a human cognition assessment system comprising one or more computers, for use by a clinician in assessing cognitive impairment of the person.

16. A system comprising:
a user device; and
one or more computers, including hardware, programmed to interact with the user device and to perform operations comprising:
receiving data comprising a person's responses regarding judgments of semantic similarities between items selected from a group of items falling into a same categorical level;
processing the data to determine a measure of distance within a generated representation of the person's responses regarding the judgments of semantic similarities, wherein the processing comprises (i) transforming the responses regarding the judgments of semantic similarities into a spatial representation, and (ii) applying a spatial randomness metric to the spatial representation, wherein the spatial randomness metric comprises a ratio of observed mean nearest neighbor distance for the responses represented in the spatial representation to a mean nearest neighbor distance expected for random responses within the spatial representation; and
generating a quantitative score of executive function for the person based at least in part on the determined measure of distance within the generated representation regarding the judgments of semantic similarities, wherein the generating comprises using (i) measured degrees of spatial randomness for responses of one or more groups of people to judgments of semantic similarities and (ii) delayed free recall responses by the one or more groups of people of items presented for judgments of semantic similarities, and providing the quantitative score of executive function, to the user device of a human cognition assessment system comprising the one or more computers, for use by a clinician in assessing cognitive impairment of the person.

17. The system of claim 16, wherein the one or more computers comprise a server system programmed to interact with the user device through a data communication network, and the user device is programmed to interact with the server as a client.

18. The system of claim 16, wherein the user device comprises a user interface device, the one or more computers comprise the user interface device, and the generating comprises outputting the score to a device comprising a non-transitory computer-readable medium.

19. The system of claim 16, wherein the transforming comprises using a multidimensional scaling method applied to a proximity matrix generated for a subset of a group of people, wherein the proximity matrix indicates distances between each pair of the items of the group of items, and each of the distances are measured by how many times another item was selected as odd-one-out when presented with the corresponding pair.

20. The system of claim 19, wherein the applying comprises determining nearest-neighbor distances (i) within the spatial representation generated using the multidimensional scaling method and (ii) within generated configurations having points placed randomly within a multidimensional space associated with the multidimensional scaling method.

21. The computer-readable medium of claim 15, wherein the response determinism parameter assigns probabilities that vary exponentially with semantic similarities indicated by the multidimensional scaling representation, and wherein the probabilities are modeled to vary by individual between (i) full correspondence with the multidimensional scaling representation regarding the judgments of the semantic similarities and (ii) random responses that are uncorrelated with the semantic similarities.

22. The computer-readable medium of claim 21, wherein the data further comprises delayed free recall responses by the person of items presented for the judgments of semantic similarities, and wherein the data comprises:

for the triadic comparisons, subject responses, response time per triad, items used for each triad, and their order of presentation per triad; and for the delayed free recall, items recalled, order of recall, response time per item recalled, repetitions and intrusions.

23. The computer-readable medium of claim 21, wherein the group of items falling into the same categorical level is animals.

24. The computer-readable medium of claim 23, wherein the animals are antelope, beaver, camel, cat, chimpanzee, chipmunk, cow, deer, dog, elephant, giraffe, goat, gorilla, horse, lion, monkey, rabbit, rat, sheep, tiger, and zebra.

25. The computer-readable medium of claim 23, wherein the animals selected from the group are nine animals selected from a group of twenty one animals and presented over twelve triadic comparisons.

* * * * *